US009926559B2

(12) United States Patent
Bennett et al.

(10) Patent No.: US 9,926,559 B2
(45) Date of Patent: Mar. 27, 2018

(54) COMPOSITIONS AND METHODS FOR MODULATION OF SMN2 SPLICING IN A SUBJECT

(71) Applicant: Biogen MA Inc., Cambridge, MA (US)

(72) Inventors: C. Frank Bennett, Carlsbad, CA (US); Gene Hung, San Diego, CA (US); Frank Rigo, Carlsbad, CA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 14/760,171

(22) PCT Filed: Jan. 9, 2014

(86) PCT No.: PCT/US2014/010930
§ 371 (c)(1),
(2) Date: Jul. 9, 2015

(87) PCT Pub. No.: WO2014/110291
PCT Pub. Date: Jul. 17, 2014

(65) Prior Publication Data
US 2016/0002627 A1    Jan. 7, 2016

Related U.S. Application Data

(60) Provisional application No. 61/750,767, filed on Jan. 9, 2013, provisional application No. 61/793,136, filed on Mar. 15, 2013, provisional application No. 61/821,615, filed on May 9, 2013, provisional application No. 61/834,818, filed on Jun. 13, 2013, provisional application No. 61/880,079, filed on Sep. 19, 2013, provisional application No. 61/886,558, filed on Oct. 3, 2013.

(51) Int. Cl.
| | | |
|---|---|---|
| C12N 15/11 | (2006.01) | |
| C12N 15/113 | (2010.01) | |
| A61B 5/04 | (2006.01) | |
| A61B 5/0488 | (2006.01) | |
| A61K 9/00 | (2006.01) | |
| A61K 31/185 | (2006.01) | |
| A61K 31/7088 | (2006.01) | |
| A61K 35/545 | (2015.01) | |
| A61K 38/30 | (2006.01) | |
| A61K 45/06 | (2006.01) | |
| A61K 47/46 | (2006.01) | |
| A61K 48/00 | (2006.01) | |
| C12Q 1/68 | (2018.01) | |
| G01N 33/50 | (2006.01) | |

(52) U.S. Cl.
CPC ........ *C12N 15/113* (2013.01); *A61B 5/04012* (2013.01); *A61B 5/0488* (2013.01); *A61K 9/0019* (2013.01); *A61K 9/0085* (2013.01); *A61K 31/185* (2013.01); *A61K 31/7088* (2013.01); *A61K 35/545* (2013.01); *A61K 38/30* (2013.01); *A61K 45/06* (2013.01); *A61K 47/46* (2013.01); *A61K 48/00* (2013.01); *C12Q 1/6883* (2013.01); *G01N 33/5091* (2013.01); *C12N 2310/11* (2013.01); *C12N 2310/315* (2013.01); *C12N 2310/322* (2013.01); *C12N 2310/351* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,176,996 A | 1/1993 | Hogan et al. |
| 5,256,775 A | 10/1993 | Froehler |
| 5,294,564 A | 3/1994 | Karapiperis et al. |
| 5,627,274 A | 5/1997 | Kole et al. |
| 5,801,154 A | 9/1998 | Baracchini et al. |
| 6,172,216 B1 | 1/2001 | Bennett et al. |
| 6,214,986 B1 | 4/2001 | Bennett et al. |
| 6,376,508 B1 | 4/2002 | Li et al. |
| 6,582,908 B2 | 6/2003 | Fodor et al. |
| 6,753,423 B1 | 6/2004 | Cook et al. |
| 6,770,633 B1 | 8/2004 | Robbins et al. |
| 6,962,906 B2 | 11/2005 | Efimov et al. |
| 7,034,009 B2 | 4/2006 | Pavco et al. |
| 7,053,207 B2 | 5/2006 | Wengel |
| 7,838,657 B2 | 11/2010 | Singh et al. |
| 8,110,560 B2 | 2/2012 | Singh et al. |

(Continued)

FOREIGN PATENT DOCUMENTS

| | | |
|---|---|---|
| WO | WO 94/26887 | 11/1994 |
| WO | WO 95/22980 | 8/1995 |
| WO | WO 01/09311 | 2/2001 |
| WO | WO 02/38738 | 5/2002 |
| WO | WO 2004/113867 | 12/2004 |
| WO | WO 2007/002390 | 1/2007 |
| WO | WO 2009/120700 | 10/2009 |
| WO | WO 2010/091308 | 8/2010 |
| WO | WO 2010/123594 | 10/2010 |
| WO | WO 2011/032109 | 3/2011 |
| WO | WO 2013/009703 | 1/2013 |

OTHER PUBLICATIONS

Batrakova et al., "Mechanism of Plutonic Effect on P-Glycoprotein Efflux System in Blood-Brain Barrier: Contributions of Energy Depletion and Membrane Fluidization" The Journal of Pharmacology and Experimental Therapeutics (2001) 299(2):483-493.

(Continued)

*Primary Examiner* — Kate Poliakova-Georgantas
(74) *Attorney, Agent, or Firm* — Fish & Richardson P.C.

(57) ABSTRACT

Disclosed herein are compounds, compositions and methods for modulating splicing of SMN2 mRNA in a subject. Also provided are uses of disclosed compounds and compositions in the manufacture of a medicament for treatment of diseases and disorders, including spinal muscular atrophy.

10 Claims, 1 Drawing Sheet

(56) References Cited

U.S. PATENT DOCUMENTS

| | | | |
|---|---|---|---|
| 8,183,002 B2 | 5/2012 | Adamczyk et al. | |
| 8,361,977 B2 | 1/2013 | Baker et al. | |
| 8,586,559 B2 | 11/2013 | Singh et al. | |
| 8,946,183 B2 | 2/2015 | Baker et al. | |
| 8,980,853 B2 | 3/2015 | Bennett et al. | |
| 2001/0053519 A1 | 12/2001 | Fodor et al. | |
| 2003/0228597 A1 | 12/2003 | Cowsert et al. | |
| 2007/0031844 A1 | 2/2007 | Khvorova et al. | |
| 2007/0292408 A1 | 12/2007 | Singh et al. | |
| 2007/0299021 A1 | 12/2007 | Dunckley et al. | |
| 2008/0045456 A1 | 2/2008 | Greenway et al. | |
| 2010/0081627 A1 | 4/2010 | Sampath et al. | |
| 2010/0087511 A1 | 4/2010 | Singh et al. | |
| 2012/0021515 A1 | 1/2012 | Swayze et al. | |
| 2012/0059042 A1* | 3/2012 | Platenburg | C12N 15/113 514/44 A |
| 2012/0087869 A1 | 4/2012 | Thakker et al. | |
| 2012/0149757 A1 | 6/2012 | Krainer et al. | |
| 2012/0190728 A1 | 7/2012 | Bennett et al. | |
| 2013/0109091 A1 | 5/2013 | Baker et al. | |
| 2014/0367278 A1 | 12/2014 | Zaworski et al. | |
| 2015/0353929 A1 | 12/2015 | Baker et al. | |
| 2017/0088835 A1 | 3/2017 | Baker et al. | |

OTHER PUBLICATIONS

Baughan et al., "Delivery of bifunctional RNAs tha target an intronic repressor and increase SMN levels in an animal model of spinal muscular atrophy" Human Molecular Genetics (2009) 18(9):1600-1611.

Branch et al., "A good antisense molecule is hard to find," TIBS (1998) 23:45-50.

Brichta et al., "Valproic acid increases the SMN2 protein level: a well-known drug as a potential therapy for spinal muscular atrophy" Human Molecular Genetics (2003) 12(19):2481-2489.

Cartegni et al., "Correction of disease-associated exon skipping by synthetic exon-specific activators" Nat. Struct. Biol. (2003) 10:120-125.

Cartegni et al., "Disruption of an SF2/ASF-dependent exonic splicing enhancer in SMN2 causes spinal muscular atrophy in the absence of SMN1", Nat. Genet., (2002) 30:377-384.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Coady et al.,"Development of a single vector system that enhances trans-splicing of SMN2 transcripts." PLoS ONE (2008) 3(10): e3468.

Crooke et al., "Basic Principles of Antisense Therapeutics" Antisense Research and Application (1998) Chapter 1:1-50.

Crooke, "Antisense strategies" Curr. Mol. Med. (2004) 4(5):465-487.

Dokka et al., "Novel non-endocyte delivery of antisense oligonucleotides" Advanced Drug Delivery Reviews (2000) 44:35-49.

Dominski et al., "Restoration of correct splicing in thalassemic pre-mRNA by antisense oligonucleotides" PNAS (1993) 90:8673-8677.

Dunckley et al., "Modification of splicing in the dystrophin gene in cultured mdx muscle cells by antisense oligoribonucleotides" Human Mol. Genetics (1998) 7(7):1083-1090.

Dunckley et al., "Modulation of Splicing in the DMD Gene by Antisense Oligoribonucleotides" Nucleosides & Nucleotides (1997) 16(7-9):1665-1668.

Efimov et al., "Phosphono Peptide Nucleic Acids with a Constrained Hydroxproline-Based Backbone" Nucleosides, Nucleotides & Nucleic Acids (2003) 22(5-8):593-599.

Forte et al., "Small interfering RNAs and Antisense Oligonucleotides for Treatment of Neurological Diseases" Current Drug Targets (2005) 6:21-29.

Friedman et al., "Correction of Aberrant Splicing of the Cystic Fibrosis Transmembrane Conductance Regulator (CFTR) Gene by Antisense Oligonucleotides" J. Biol. Chem. (1999) 274:36193-36199.

Gravrilina et al., "Neuronal SMN expression corrects spinal muscular atrophy in severe SMA mice while muscle-specific SMN expression has no phenotypic effect" Hum Mol Genet (2008) 17(8):1063-1075.

Heasman, "Morpholino Oligos: Making Sense of Antisense?" Developmental Biology (2002) 243:209-214.

Hofmann et al., "Htra2-beta1 stimulates an exonic splicing enhancer and can restor full-length SMN expression to survival motor neuron 2 (SMN2)" PNAS (2000) 97(17):9618-9623.

Hua et al., "Antisense correction of SMN2 splicing in the CNS rescues necrosis in a type III SMA mouse model" Genes Dev. (2010) 24:1634-1644.

Hua et al., "Antisense masking of an hnRNP A1/A2 inronic splicing silencer corrects SMN2 splicing in transgenic mice" American Journal of Human Genetics (2008) 82(4):834-848.

Hua et al., "Enhancement of SMN2 exon 7 inclusion by antisense oligonucleotides targeting the exon" PLOS Biology (2007) 5(4):E73.

Ittig et al., "Nuclear antisense effects in cyclophilin A pre-mRNA splicing by oligonucleotides: a comparison of tricyclo-DNA with LNA" Nucleic Acids Research (2004) 32(10:346-353.

Jaeger et al., "Transport of Antisense Across the Blood-Brain Barrier" Methods in Molecular Medicine (2005) vol. 106: Antisense Therapeutics, Second Edition, I. Phillips (Ed.) Humana Press, Inc. Totowa, N. J., Cht. 12:237-251.

Kashima et al., "A negative element in SMN2 exon 7 inhibits splicing in spinal muscular atrophy." Nature Genetics (2003) 34(4):460-463.

Kobayashi et al., "Utility of Survival Motor Neuron ELISA for Spinal Muscular Atrophy Clinical and Preclinical Analyses," PLoS ONE (2011) 6:e24269 pp. 1-15.

Kole et al., "RNA modulation, repair and remodeling by splice switching oligonucleotides" Acta Biochimica Polonica (2004) 51(2):373-378.

Kole, "Modification of pre-mRNA splicing by antisense oligonucleotides" Acta Biochimica Polonica (1997) 44(2):231-238.

Krawczak et al., "The mutational spectrum of single base-pair substitutions in mRNA splice junctions of human genes: causes and consequences." Hum. Genet. (1992) 90:41-54.

Kurreck, "Antisense Technologies Improvement Through Novel Chemical Modifications" European Journal of Biochemistry (2003) 270(8):1628-1644.

Lacerra et al., "Restoration of hemoglobin A synthesis in erythroid cells from peripheral blood of thalassemic patients" PNAS (2000) 97(17):9591-9596.

Le et al., "SMNdelta7, the major product of the centromeric survival motor neuron (SMN2) gene, exends survival in mice with spinal muscular atrophy and associates with full-length SMN" Human Molecular Genetics (2005) 14(6):845-857.

Lefebvre et al., "The Role of the SMN Gene in Proximal Spinal Muscular Atrophy" Hum. Mol. Genet. (1998) 7(10):1531-1536.

Lim et al., "Modulation of Survival Motor Neuron Pre-mRNA Splicing by Inhibition of Alternative 3'Splice Site Pairing" J. Biol. Chem. (2001) 276(48):45476-45483.

Lorson et al., "A single nucleotide in the SMN gene regulates splicing and is responsible for spinal muscular atrophy" PNAS (1999) 96:6307-6311.

Lu et al., "Systemic delivery of antisense oligoribonucleotide restores dystrophin expression in body-wide skeletal muscles" PNAS (2005) 102(1):198-203.

Madocsai et al., "Correction of SMN2 Pre-mRNA Splicing by Antisense U7 Small Nuclear RNAs" Molecular Therapy (2005) 12(6):1013-1022.

Matsuzawa et al., "Age-related volumetric changes of brain gray and white matter in healthy infants and children." Cereb Cortex (2001) 11(4):335-342.

Miyajima et al., "Identification of a Cis-Acting Element for the Regulation of SMN Exon 7 Splicing" J. Biol. Chem. (2002) 277(26):23271-23277.

(56) References Cited

OTHER PUBLICATIONS

Miyaso et al., "An Intronic Splicing Enhancer Element in Survival Motor Neuron (SMN) Pre-mRNA" J. Biol. Chem. (2003) 278(18):15825-15831.
New England Biolabs 1998/99 Catalog (cover page and pp. 121 and 284).
Ouagazzal, Abdel-Mouttalib. "Reducing Gene Expression in the Brain via Antisense Methods." Current Protocols in Neuroscience. Hoboken: John Wiley & Sons, 2001. N.Chapter 5.
Passini et al., "CNS-targeted gene therapy improves survival and motor function in a mouse model of spinal muscular atrophy" J Clin Invest (2010) 120(4): 1253-64.
Rebuffat et al., "Gene delivery by a steroid-peptide nucleic acid conjugate" FASEB J. (2002) 19(11):1426-1428.
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Sazani et al., "Therapeutic potential of antisense oligonucleotides as modulators of alternative splicing" The Journal of Clinical Investigation (2003) 112(4):481-486.
Schmid et al., "Animal models of spinal muscular atrophy" Journal of Child Neurology (2007) 22(8):1004-1012.
Sierakowska et al., "Restoration of β-Globin Gene Expression in Mammalian Cells by Antisense Oligonucleotides That Modify the Aberrant Splicing Patierns of Thalassemic Pre-mRNAs" Nucleosides & Nucleotides (1997) 16(7-9):1173-1182.
Sierakowska et al., "Repair of thalassemic human β-globin mRNA in mammalian cells by antisense oligonucleotides" PNAS (1996) 93:12840-12844.
Singh et al., "A short antisense oligonucleotide masking a unique intronic motif prevents skipping of a critical exon in spinal muscular atrophy" RNA Bio (2009) 6(3):341-350.
Singh et al., "In vivo selection reveals combinatorial controls that define a critical exon in the spinal muscular atrophy genes" RNA (2004) 10:1291-1305.
Singh et al., "An extended inhibitory context causes skipping of exon 7 of SMN2 in spinal muscular atrophy" Biochem. Biophys. Res. Comm. (2004) 315(2):381-388.
Singh et al., "Splicing of a critical exon of human Survival Motor Neuron is regulated by a unique silencer element located in the last intron" Molecular and Cellular Biology (2006) 26(4):1333-1346.
Skordis et al., "Bifunctional Antisense Oligonucleotides Provide a Trans-Acting Splicing Enhancer that Stimulated SMN2 Gene Expression in Patient Fibroblasts" PNAS (2003) 100(7):4114-4119.
Smith "Antisense oligonucleotide therapy for neurodegenerative disease" Journal of Clinical Investigation (2006) 116:2290-2296.
Takeshima et al., "Modulation of in vitro splicing of the upstream intron by modifying an intra-exon sequence which is deleted from the dystrophin gene in dystrophin Kobe." J. Clin. Invest. (1995) 95(2):515-520.
Taylor et al., "Induction of endogenous Bcl-xS through the control of Bcl-x pre-mRNA splicing by antisense oligonucleotides" Nat. Biotechnol. (1999) 17:1097-1100.

Translated abstract from JP 2004-344072.
Veldink et al., "SMN genotypes producing less SMN protein increase susceptibility to and severity of sporadic ALS" Neurology (2005) 65(6):820-825.
Vinogradov et al., "Nanogels for Oligonucleotide Delivery to the Brain" Bioconjugate Chem. (2004) 15:50-60.
Wahlestedt et al., "Potent and nontoxic antisense oligonucleotides containined locked nucleic acids" PNAS (2000) 97(10):5633-5638.
Wang, "Antisense oligodeoxynucleotides selectively suppress expression of the mutant alpha 2(I) collagen allele in type IV osteogenesis imperfecta fibroblasts. A molecular approach to therapeutics of dominant negative disorders." J. Clin. Invest. (1996) 97(2):448-454.
Williams et al., "Oligonucleotide-mediated survival of motor neuron protein expression in CNS improves phenotype in a mouse model of Spinal Muscular Atrophy" Journal of Neuroscience (2009) 29(24):7633-7638.
Wilton et al., "Specific removal of the nonsense mutation from the mdx dystrophin mRNA using antisense oligonucleotides" Neuromuscul. Disord (1999) 9:330-338.
Yeo et al., "Variation in sequence and organization of splicing regulatory elements in vertebrate genes." Proc. Natl. Acad. Sci. (2004) 101(44):15700-15705.
European Search Report for application EP 06773838 dated Aug. 11, 2010.
European Search Report for application EP 10790221 dated Sep. 4, 2013.
International Search Report for application PCT/US06/24469 dated Sep. 13, 2007.
International Search Report for application PCT/US10/30940 dated Jul. 13, 2010.
International Search Report for application PCT/US2010/39077 dated Aug. 17, 2010.
U.S. Appl. No. 15/267,408, filed Sep. 16, 2016, Baker et al.
U.S. Appl. No. 14/617,388, filed Feb. 9, 2015, Bennett et al.
U.S. Appl. No. 15/303,829, filed Oct. 13, 2016, Rigo et al.
International Search Report and Written Opinion for application PCT/US2015/026326 dated Nov. 3, 2015, 10 pages.
International Search Report and Written Opinion for application PCT/US2015/049598 dated Jan. 19, 2016, 10 pages.
Hua et al., "Peripheral SMN restoration is essential for long-term rescue of a severe spinal muscular atrophy mouse model," Nature (2011) 478: 123-126.
Passini et al., "Antisense Oligonucleotides Delivered to the Mouse CNS Ameliorate Symptoms of Severe Spinal Muscular Atrophy," Science Translational Medicine (2011) 72: 72ra18-72ra18.
Swoboda et al., "0.9 First-in-human phase I study to assess safety, tolerability and dose for intrathecal injection of ISIS-SMNRx in SMA patients," Neuromuscular Disorders (2013) 23: 797-798.
European Search Report for application EP 2943225 dated Jun. 10, 2016.
SPINRAZA (nusinersen) injection, for intrathecal use, FDA Label, Dec. 2016, 13 pages.

* cited by examiner

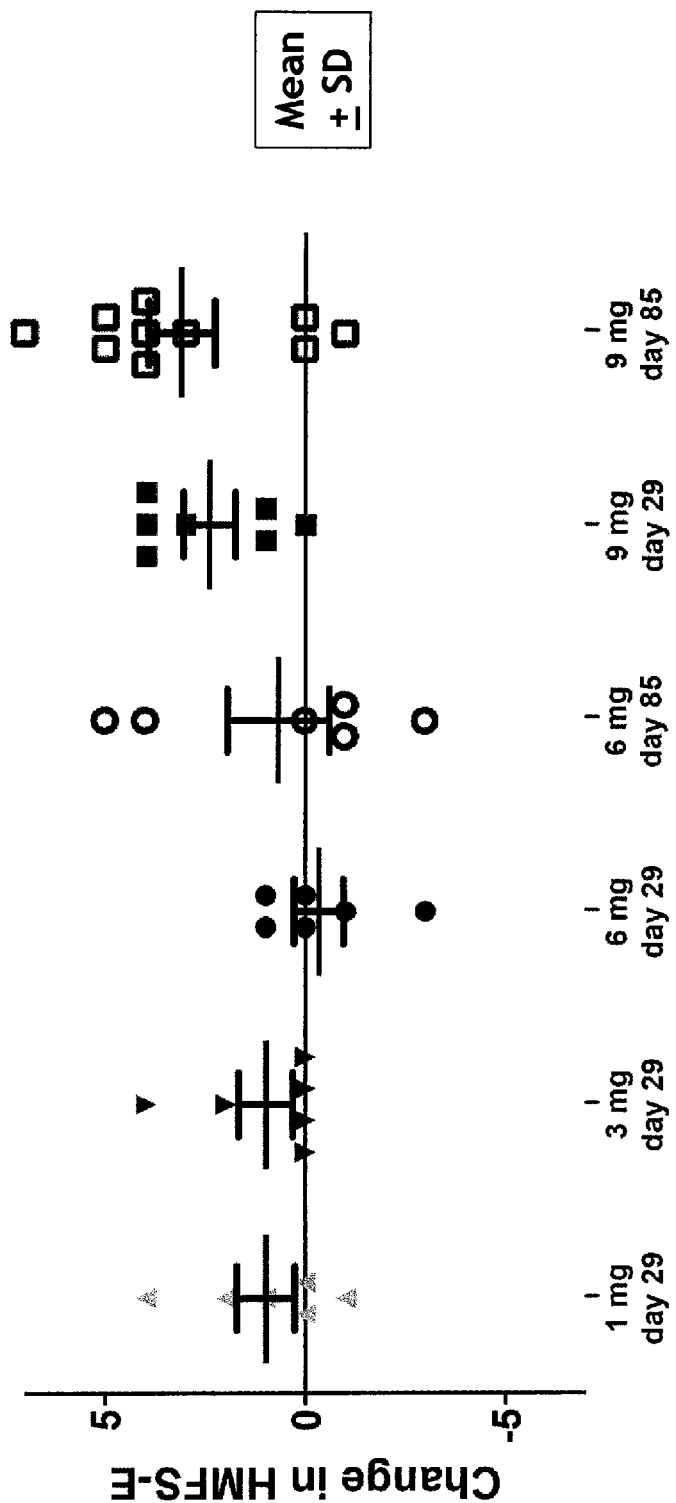

SEQUENCE LISTING

```
<160> NUMBER OF SEQ ID NOS: 24

<210> SEQ ID NO 1
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1
tcactttcat aatgctgg                                                 18

<210> SEQ ID NO 2
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 2
tttcataatg ctggc                                                    15

<210> SEQ ID NO 3
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 3
tgctggcaga cttac                                                    15

<210> SEQ ID NO 4
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 4
cataatgctg gcaga                                                    15

<210> SEQ ID NO 5
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 5
tcataatgct ggcag                                                    15

<210> SEQ ID NO 6
<211> LENGTH: 15
<212> TYPE: DNA
<213> ORGANISM: Artificial sequence
<220> FEATURE:
```

<223> OTHER INFORMATION: Synthetic oligonucleotide

<400> SEQUENCE: 6
ttcataatgc tggca                                              15

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
attcactttc ataatgctgg                                         20

<210> SEQ ID NO 8
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 8
ctttcataat gctgg                                              15

<210> SEQ ID NO 9
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 9
tcataatgct gg                                                 12

<210> SEQ ID NO 10
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 10
actttcataa tgctg                                              15

<210> SEQ ID NO 11
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 11
ttcataatgc tg                                                 12

<210> SEQ ID NO 12
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 12
cactttcata atgct                                              15

```
<210> SEQ ID NO 13
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 13
tttcataatg ct                                                        12

<210> SEQ ID NO 14
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 14
tcactttcat aatgc                                                     15

<210> SEQ ID NO 15
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 15
ctttcataat gc                                                        12

<210> SEQ ID NO 16
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 16
ttcactttca taatg                                                     15

<210> SEQ ID NO 17
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 17
actttcataa tg                                                        12

<210> SEQ ID NO 18
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 18
attcactttc ataat                                                     15

<210> SEQ ID NO 19
<211> LENGTH: 12
<212> TYPE: DNA
<213> ORGANISM: Artificial sequence
<220> FEATURE:
<223> OTHER INFORMATION: Synthetic oligonucleotide
```

```
<400> SEQUENCE: 19
cactttcata at                                                     12

<210> SEQ ID NO 20
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 20
gattcacttt cataa                                                  15

<210> SEQ ID NO 21
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 21
tcactttcat aa                                                     12

<210> SEQ ID NO 22
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 22
ttcactttca ta                                                     12

<210> SEQ ID NO 23
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 23
attcactttc at                                                     12

<210> SEQ ID NO 24
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 24
agtaagattc acttt                                                  15
```

US 9,926,559 B2

COMPOSITIONS AND METHODS FOR MODULATION OF SMN2 SPLICING IN A SUBJECT

SEQUENCE LISTING

The present application is being filed along with a Sequence Listing in electronic format. The Sequence Listing is provided as a file entitled CORE0108USASEQ_ST25.txt, created Jul. 9, 2015, which is 8 Kb in size. The information in the electronic format of the sequence listing is incorporated herein by reference in its entirety.

BACKGROUND OF THE INVENTION

Newly synthesized eukaryotic mRNA molecules, known as primary transcripts or pre-mRNA are processed before translation. Processing of the pre-mRNAs includes addition of a 5' methylated cap and an approximately 200-250 base poly(A) tail to the 3' end of the transcript. Processing of mRNA from pre-mRNA also frequently involves splicing of the pre-mRNA, which occurs in the maturation of 90-95% of mammalian mRNAs. Introns (or intervening sequences) are regions of a pre-mRNA (or the DNA encoding it) that are not included in the coding sequence of the mature mRNA. Exons are regions of a primary transcript that remain in the mature mRNA. The exons are spliced together to form the mature mRNA sequence. Splice junctions are also referred to as splice sites with the 5' side of the junction often called the "5' splice site," or "splice donor site" and the 3' side the "3' splice site" or "splice acceptor site." In splicing, the 3' end of an upstream exon is joined to the 5' end of the downstream exon. Thus the unspliced pre-mRNA has an exon/intron junction at the 5' end of an intron and an intron/exon junction at the 3' end of an intron. After the intron is removed, the exons are contiguous at what is sometimes referred to as the exon/exon junction or boundary in the mature mRNA. Cryptic splice sites are those which are less often used but may be used when the usual splice site is blocked or unavailable. Alternative splicing, defined as the splicing together of different combinations of exons, often results in multiple mRNA transcripts from a single gene.

Up to 50% of human genetic diseases resulting from a point mutation result in aberrant pre-mRNA processing. Such point mutations can either disrupt a current splice site or create a new splice site, resulting in mRNA transcripts comprised of a different combination of exons or with deletions in exons. Point mutations also can result in activation of a cryptic splice site or disrupt regulatory cis elements (i.e. splicing enhancers or silencers) (Cartegni et al., Nat. Rev. Genet., 2002, 3, 285-298; Drawczak et al., Hum. Genet., 1992, 90, 41-54). Antisense oligonucleotides have been used to target mutations that lead to aberrant splicing in several genetic diseases in order to redirect splicing to give a desired splice product (Kole, Acta Biochimica Polonica, 1997, 44, 231-238).

Antisense compounds have also been used to alter the ratio of naturally occurring alternate splice variants such as the long and short forms of Bcl-x pre-mRNA (U.S. Pat. No. 6,172,216; U.S. Pat. No. 6,214,986; Taylor et al., Nat. Biotechnol. 1999, 17, 1097-1100) or to force skipping of specific exons containing premature termination codons (Wilton et al., Neuromuscul. Disord., 1999, 9, 330-338). U.S. Pat. No. 5,627,274 and WO 94/26887 disclose compositions and methods for combating aberrant splicing in a pre-mRNA molecule containing a mutation using antisense oligonucleotides which do not activate RNAse H.

Proximal spinal muscular atrophy (SMA) is a genetic, neurodegenerative disorder characterized by the loss of spinal motor neurons. SMA is an autosomal recessive disease of early onset and is currently the leading cause of death among infants. The severity of SMA varies among patients and has thus been classified into three types. Type I SMA is the most severe form with onset at birth or within 6 months and typically results in death within 2 years. Children with type I SMA are unable to sit or walk. Type II SMA is the intermediate form and patients are able to sit, but cannot stand or walk. Patients with type III SMA, a chronic form of the disease, typically develop SMA after 18 months of age (Lefebvre et al., Hum. Mol. Genet., 1998, 7, 1531-1536).

The molecular basis of SMA is caused by the loss of both copies of survival motor neuron gene 1 (SMN1), which may also be known as SMN Telomeric, a protein that is part of a multi-protein complex thought to be involved in snRNP biogenesis and recycling. A nearly identical gene, SMN2, which may also be known as SMN Centromeric, exists in a duplicated region on chromosome 5q13 and modulates disease severity. Expression of the normal SMN1 gene results solely in expression of survival motor neuron (SMN) protein. Although SMN1 and SMN2 have the potential to code for the same protein, SMN2 contains a translationally silent mutation at position +6 of exon 7, which results in inefficient inclusion of exon 7 in SMN2 transcripts. Thus, the predominant form of SMN2 is a truncated version, lacking exon 7, which is unstable and inactive (Cartegni and Krainer, Nat. Genet., 2002, 30, 377-384). Expression of the SMN2 gene results in approximately 10-20% of the SMN protein and 80-90% of the unstable/non-functional SMN-delta7 protein. SMN protein plays a well-established role in assembly of the spliceosome and may also mediate mRNA trafficking in the axon and nerve terminus of neurons.

Antisense technology is an effective means for modulating the expression of one or more specific gene products, including alternative splice products, and is uniquely useful in a number of therapeutic, diagnostic, and research applications. The principle behind antisense technology is that an antisense compound, which hybridizes to a target nucleic acid, modulates gene expression activities such as transcription, splicing or translation through one of a number of antisense mechanisms. The sequence specificity of antisense compounds makes them extremely attractive as tools for target validation and gene functionalization, as well as therapeutics to selectively modulate the expression of genes involved in disease.

Certain antisense compounds complementary to SMN2 are known in the art. See for example, WO 2007/002390; U.S. 61/168,885; Hua et al., American J. of Human Genetics (April 2008) 82, 1-15; Singh et al., RNA Bio. 6:3, 1-10 (2009). Certain antisense compounds and methods disclosed herein posses desirable characteristics compared to such compounds and methods known in the art. Chimeric peptide nucleic acid molecules designed to modulate splicing of SMN2 have been described (WO 02/38738; Cartegni and Krainer, Nat. Struct. Biol., 2003, 10, 120-125).

SUMMARY OF THE INVENTION

In certain embodiments, the present invention provides methods comprising administering to a subject an antisense compound comprising an antisense oligonucleotide complementary to intron 7 of a nucleic acid encoding human SMN2 pre-mRNA, wherein the antisense compound is administered into the cerebrospinal fluid. In certain embodiments, the administration is into the intrathecal space. In certain embodiments, the administration is into the cerebrospinal fluid in the brain. In certain embodiments, the administration comprises a bolus injection. In certain embodiments, the administration comprises infusion with a delivery pump.

The present disclosure provides the following non-limiting numbered embodiments:

Embodiment 1

A method of treating a human patient having spinal muscular atrophy comprising administering to the human patient at least one dose of an antisense compound comprising an antisense oligonucleotide complementary to intron 7 of a nucleic acid encoding human SMN2 pre-mRNA, wherein the antisense compound is administered into the cerebrospinal fluid at a dose of 0.1 to 20 milligrams; and thereby ameliorating at least one symptom of spinal muscular atrophy in the human patient.

Embodiment 2

The method of embodiment 1, wherein the dose is from 0.1 to 15 milligrams.

Embodiment 3

The method of embodiment 1, wherein the dose is from 0.1 to 10 milligrams.

Embodiment 4

The method of embodiment 1, wherein the dose is from 0.1 to 5 milligrams.

Embodiment 5

The method of embodiment 1, wherein the dose is from 0.1 to 1 milligrams.

Embodiment 6

The method of embodiment 1, wherein the dose is from 0.1 to 0.5 milligrams.

Embodiment 7

The method of embodiment 1, wherein the dose is from 0.5 to 20 milligrams.

Embodiment 8

The method of embodiment 1, wherein the dose is from 0.5 to 15 milligrams.

Embodiment 9

The method of embodiment 1, wherein the dose is from 0.5 to 10 milligrams.

Embodiment 10

The method of embodiment 1, wherein the dose is from 0.5 to 5 milligrams.

Embodiment 11

The method of embodiment 1, wherein the dose is from 0.5 to 1 milligrams.

Embodiment 12

The method of embodiment 1, wherein the dose is from 1 to 20 milligrams.

Embodiment 13

The method of embodiment 1, wherein the dose is from 1 to 15 milligrams.

Embodiment 14

The method of embodiment 1, wherein the dose is from 1 to 10 milligrams.

Embodiment 15

The method of embodiment 1, wherein the dose is from 1 to 5 milligrams.

Embodiment 16

The method of embodiment 1, wherein the dose is from 3 to 20 milligrams.

Embodiment 17

The method of embodiment 1, wherein the dose is from 3 to 15 milligrams.

Embodiment 18

The method of embodiment 1, wherein the dose is from 3 to 10 milligrams.

Embodiment 19

The method of embodiment 1, wherein the dose is from 3 to 5 milligrams.

Embodiment 20

The method of embodiment 1, wherein the dose is from 5 to 20 milligrams.

Embodiment 21

The method of embodiment 1, wherein the dose is from 5 to 15 milligrams.

Embodiment 22

The method of embodiment 1, wherein the dose is from 5 to 10 milligrams.

Embodiment 23

The method of embodiment 1, wherein the dose is from 10 to 15 milligrams.

Embodiment 24

The method of embodiment 1, wherein the dose is from 10 to 20 milligrams.

Embodiment 25

The method of embodiment 1, wherein the dose is from 15 to 20 milligrams.

Embodiment 26

The method of embodiment 1, wherein the dose is about 0.1 milligrams.

Embodiment 27

The method of embodiment 1, wherein the dose is about 0.3 milligrams.

Embodiment 28

The method of embodiment 1, wherein the dose is about 0.5 milligrams.

Embodiment 29

The method of embodiment 1, wherein the dose is about 1 milligram.

Embodiment 30

The method of embodiment 1, wherein the dose is about 2 milligrams.

Embodiment 31

The method of embodiment 1, wherein the dose is about 3 milligrams.

Embodiment 32

The method of embodiment 1, wherein the dose is about 4 milligrams.

Embodiment 33

The method of embodiment 1, wherein the dose is about 5 milligrams.

Embodiment 34

The method of embodiment 1, wherein the dose is about 6 milligrams.

Embodiment 35

The method of embodiment 1, wherein the dose is about 7 milligrams.

Embodiment 36

The method of embodiment 1, wherein the dose is about 8 milligrams.

Embodiment 37

The method of embodiment 1, wherein the dose is about 9 milligrams.

Embodiment 38

The method of embodiment 1, wherein the dose is about 10 milligrams.

Embodiment 39

The method of embodiment 1, wherein the dose is about 11 milligrams.

Embodiment 40

The method of embodiment 1, wherein the dose is about 12 milligrams.

Embodiment 41

The method of embodiment 1, wherein the dose is about 13 milligrams.

Embodiment 42

The method of embodiment 1, wherein the dose is about 14 milligrams.

Embodiment 43

The method of embodiment 1, wherein the dose is about 15 milligrams.

Embodiment 44

The method of embodiment 1, wherein the dose is less than 20 milligrams.

Embodiment 45

The method of embodiment 1, wherein the dose is less than 15 milligrams.

Embodiment 46

The method of embodiment 1, wherein the dose is less than 10 milligrams.

Embodiment 47

The method of embodiment 1, wherein the dose is less than 5 milligrams.

Embodiment 48

The method of embodiment 1, wherein the dose is about 4.8 milligrams.

Embodiment 49

The method of embodiment 1, wherein the dose is about 5.16 milligrams.

Embodiment 50

The method of embodiment 1, wherein the dose is about 5.4 milligrams.

Embodiment 51

The method of embodiment 1, wherein the dose is about 7.2 milligrams.

Embodiment 52

The method of embodiment 1, wherein the dose is about 7.74 milligrams.

Embodiment 53

The method of embodiment 1, wherein the dose is about 8.10 milligrams.

Embodiment 54

The method of embodiment 1, wherein the dose is about 9.60 milligrams.

Embodiment 55

The method of embodiment 1, wherein the dose is about 10.32 milligrams.

Embodiment 56

The method of embodiment 1, wherein the dose is about 10.80 milligrams.

Embodiment 57

The method of embodiment 1, wherein the dose is about 11.3 milligrams.

Embodiment 58

The method of embodiment 1, wherein the dose is about 12.88 milligrams.

Embodiment 59

The method of embodiment 1, wherein the dose is about 13.5 milligrams.

Embodiment 60

The method of embodiment 1, wherein the dose is about 14.13 milligrams.

Embodiment 61

The method of any of embodiments 1-60, wherein the dose is delivered in a volume of 1 to 10 mL of a pharmaceutically acceptable diluent.

Embodiment 62

The method of any of embodiments 1-60, wherein the dose is delivered in a volume of 1 to 9 mL of a pharmaceutically acceptable diluent.

Embodiment 63

The method of any of embodiments 1-60, wherein the dose is delivered in a volume of 1 to 8 mL of a pharmaceutically acceptable diluent.

Embodiment 64

The method of any of embodiments 1-60, wherein the dose is delivered in a volume of 1 to 7 mL of a pharmaceutically acceptable diluent.

Embodiment 65

The method of any of embodiments 1-60, wherein the dose is delivered in a volume of 1 to 6 mL of a pharmaceutically acceptable diluent.

Embodiment 66

The method of any of embodiments 1-60, wherein the dose is delivered in a volume of 1 to 5 mL of a pharmaceutically acceptable diluent.

Embodiment 67

The method of any of embodiments 1-60, wherein the dose is delivered in a volume of 1 to 4 mL of a pharmaceutically acceptable diluent.

Embodiment 68

The method of any of embodiments 1-60, wherein the dose is delivered in a volume of 1 to 3 mL of a pharmaceutically acceptable diluent.

Embodiment 69

The method of any of embodiments 1-60, wherein the dose is delivered in a volume of 1 to 2 mL of a pharmaceutically acceptable diluent.

Embodiment 70

The method of any of embodiments 1-60, wherein the dose is delivered in a volume of 5 mL of a pharmaceutically acceptable diluent.

Embodiment 71

The method of any of embodiments 1-60, wherein the dose is delivered in a volume of 4 mL of a pharmaceutically acceptable diluent.

Embodiment 72

The method of any of embodiments 1-60, wherein the dose is delivered in a volume of 6 mL of a pharmaceutically acceptable diluent.

Embodiment 73

The method of any of embodiments 1-60, wherein the dose is delivered in a volume of 4.3 mL of a pharmaceutically acceptable diluent.

Embodiment 74

The method of any of embodiments 1-60, wherein the dose is delivered in a volume of 4.5 mL of a pharmaceutically acceptable diluent.

Embodiment 75

The method of any of embodiments 1-60, wherein the dose is delivered in a volume of 4.7 mL of a pharmaceutically acceptable diluent.

Embodiment 76

The method of any of embodiments 1-60, wherein the dose is delivered in a volume, wherein the volume of the pharmaceutically acceptable diluent is determined by CSF volume scaling.

Embodiment 77

The method of any of embodiments 1-60, wherein the pharmaceutically acceptable diluent is artificial CSF.

Embodiment 78

The method of any of embodiments 1-60, wherein the pharmaceutically acceptable diluent is CSF.

Embodiment 79

The method of any of embodiments 60-78, wherein the concentration of the antisense compound is 0.2 mg/mL.

Embodiment 80

The method of any of embodiments 60-78, wherein the concentration of the antisense compound is 0.6 mg/mL.

Embodiment 81

The method of any of embodiments 60-78, wherein the concentration of the antisense compound is 1.2 mg/mL.

Embodiment 82

The method of any of embodiments 60-78, wherein the concentration of the antisense compound is 1.8 mg/mL.

Embodiment 83

The method of any of embodiments 60-78, wherein the concentration of the antisense compound is 2.0 mg/mL.

Embodiment 84

The method of any of embodiments 60-78, wherein the concentration of the antisense compound is 2.2 mg/mL.

Embodiment 85

The method of any of embodiments 60-78, wherein the concentration of the antisense compound is 2.4 mg/mL.

Embodiment 86

The method of any of embodiments 60-78, wherein the concentration of the antisense compound is 2.6 mg/mL.

Embodiment 87

The method of any of embodiments 60-78, wherein the concentration of the antisense compound is 2.7 mg/mL.

Embodiment 88

The method of any of embodiments 60-78, wherein the concentration of the antisense compound is 2.8 mg/mL.

Embodiment 89

The method of any of embodiments 60-78, wherein the concentration of the antisense compound is 2.9 mg/mL.

Embodiment 90

The method of any of embodiments 60-78, wherein the concentration of the antisense compound is 3.0 mg/mL.

Embodiment 91

The method of any of embodiments 60-78, wherein the concentration of the antisense compound is 3.1 mg/mL.

Embodiment 92

The method of any of embodiments 60-78, wherein the concentration of the antisense compound is 3.2 mg/mL.

Embodiment 93

The method of any of embodiments 60-78, wherein the concentration of the antisense compound is 3.3 mg/mL.

Embodiment 94

The method of any of embodiments 60-78, wherein the antisense compound consists of ISIS 396443.

Embodiment 95

The method of any of embodiments 1-94, wherein the dose is an equivalent dose.

Embodiment 96

The method of any of embodiments 1-94, wherein the dose is an adjusted dose.

Embodiment 97

The method of embodiment 96, wherein the adjusted dose is determined by CSF volume scaling.

Embodiment 98

The method of any of embodiments 1-97, wherein the administration is into the intrathecal space.

Embodiment 99

The method of any of embodiments 1-98, wherein the administration is into the intrathecal space between the L3 and L4 vertebrae.

Embodiment 100

The method of any of embodiments 1-98, wherein the administration is into the intrathecal space between the L2 and L3 vertebrae.

Embodiment 101

The method of any of embodiments 1-98, wherein the administration is into the intrathecal space between the L4 and L5 vertebrae.

Embodiment 102

The method of any of embodiments 1-98, wherein the administration is into the intrathecal space between the L5 and L6 vertebrae.

Embodiment 103

The method of any of embodiments 1-102, wherein the administration is by a bolus injection.

Embodiment 104

The method of any of embodiments 1-103, wherein the administration is by infusion with a delivery pump.

Embodiment 105

The method of any of embodiments 1-104, wherein the administration is by lumbar puncture.

Embodiment 106

The method of any of embodiments 1-105, wherein the administration is through a 21, 22, 23, 24, or 25 gauge needle.

Embodiment 107

The method of any of embodiments 1-105, wherein the administration is through a 21 gauge needle.

Embodiment 108

The method of any of embodiments 1-105, wherein the administration is through a 22 gauge needle.

Embodiment 109

The method of any of embodiments 1-105, wherein the administration is through a 23 gauge needle.

Embodiment 110

The method of any of embodiments 1-105, wherein the administration is through a 24 gauge needle.

Embodiment 111

The method of any of embodiments 1-105, wherein the administration is through a 25 gauge needle.

Embodiment 112

The method of any of embodiments 106-111, wherein the needle is a spinal anesthesia needle.

Embodiment 113

The method of any of embodiments 1-112 comprising administering a series of at least two doses.

Embodiment 114

The method of any of embodiments 1-112 comprising administering a series of at least three doses.

Embodiment 115

The method of any of embodiments 1-112 comprising administering a series of at least four doses.

Embodiment 116

The method of any of embodiments 113-115, wherein the doses are administered with a dose frequency of about two weeks between doses.

Embodiment 117

The method of any of embodiments 113-115, wherein the doses are administered with a dose frequency of about three weeks between doses.

Embodiment 118

The method of any of embodiments 113-115, wherein the doses are administered with a dose frequency of about four weeks between doses.

Embodiment 119

The method of any of embodiments 113-115, wherein the doses are administered with a dose frequency of about five weeks between doses.

Embodiment 120

The method of any of embodiments 113-115, wherein the doses are administered with a dose frequency of about six weeks between doses.

Embodiment 121

The method of any of embodiments 113-115, wherein the doses are administered with a dose frequency of about seven weeks between doses.

Embodiment 122

The method of any of embodiments 113-115, wherein the doses are administered with a dose frequency of about eight weeks between doses.

Embodiment 123

The method of any of embodiments 113-115, wherein the doses are administered with a dose frequency of about three months between doses.

Embodiment 124

The method of any of embodiments 113-115, wherein the doses are administered with a dose frequency of about four months between doses.

Embodiment 125

The method of any of embodiments 113-115, wherein the doses are administered with a dose frequency of about six months between doses.

Embodiment 126

The method of any of embodiments 113-115, wherein the doses are administered with a dose frequency of about 11 months between doses.

Embodiment 127

The method of any of embodiments 113-115, wherein the doses are administered with a dose frequency of about 12 months between doses.

Embodiment 128

The method of any of embodiments 113-115, wherein the doses are administered with a dose frequency of about 13 months between doses.

Embodiment 129

The method of any of embodiments 113-115, wherein the doses are administered with a dose frequency of about 14 months between doses.

Embodiment 130

The method of any of embodiments 113-115, wherein the doses are administered with a dose frequency of about 15 months between doses.

Embodiment 131

The method of any of embodiments 113-115, wherein the doses are administered with a dose frequency of at least one month between doses.

Embodiment 132

The method of any of embodiments 113-115, wherein the doses are administered with a dose frequency of at least two months between doses.

Embodiment 133

The method of any of embodiments 113-115, wherein the doses are administered with a dose frequency of at least three months between doses.

Embodiment 134

The method of any of embodiments 113-115, wherein the doses are administered with a dose frequency of at least four months between doses.

Embodiment 135

The method of any of embodiments 113-115, wherein the doses are administered with a dose frequency of at least five months between doses.

Embodiment 136

The method of any of embodiments 113-115, wherein the doses are administered with a dose frequency of at least six months between doses.

Embodiment 137

The method of any of embodiments 113-115, wherein the doses are administered with a dose frequency of at least 11 months between doses.

Embodiment 138

The method of any of embodiments 113-115, wherein the doses are administered with a dose frequency of at least 12 months between doses.

Embodiment 139

The method of any of embodiments 113-115, wherein the doses are administered with a dose frequency of at least 13 months between doses.

Embodiment 140

The method of any of embodiments 113-115, wherein the doses are administered with a dose frequency of at least 14 months between doses.

Embodiment 141

The method of any of embodiments 113-115, wherein the doses are administered with a dose frequency of at least 15 months between doses.

Embodiment 142

The method of any of embodiments 113-115, wherein the doses are administered with a dose frequency of more than six months between doses.

Embodiment 143

The method of any of embodiments 113-115, wherein a first dose is administered and wherein the second dose is administered 12-18 days after the first dose.

Embodiment 144

The method of any of embodiments 113-115, wherein a first dose is administered and wherein the second dose is administered 15 days after the first dose.

Embodiment 145

The method of any of embodiments 113-115, wherein a first dose is administered and wherein the second dose is administered 24-34 days after the first dose.

Embodiment 146

The method of any of embodiments 113-115, wherein a first dose is administered and wherein the second dose is administered 29 days after the first dose.

Embodiment 147

The method of any of embodiments 113-115, wherein a first dose is administered and wherein the second dose is administered 80-90 days after the first dose.

Embodiment 148

The method of any of embodiments 113-115, wherein a first dose is administered and wherein the second dose is administered 85 days after the first dose.

Embodiment 149

The method of any of embodiments 113-115, wherein a first dose is administered, wherein a second dose is administered 12-18 days after the first dose, and wherein a third dose is administered 80-90 days after the first dose.

Embodiment 150

The method of any of embodiments 113-115, wherein a first dose is administered, wherein a second dose is administered 24-34 days after the first dose, and wherein a third dose is administered 80-90 days after the first dose.

Embodiment 151

The method of any of embodiments 113-115, wherein a first dose is administered, wherein a second dose is administered 15 days after the first dose, and wherein a third dose is administered 80-90 days after the first dose.

Embodiment 152

The method of any of embodiments 113-115, wherein a first dose is administered, wherein a second dose is administered 29 days after the first dose, and wherein a third dose is administered 80-90 days after the first dose.

Embodiment 153

The method of any of embodiments 113-115, wherein a first dose is administered, wherein a second dose is administered 12-18 days after the first dose, and wherein a third dose is administered 85 days after the first dose.

Embodiment 154

The method of any of embodiments 113-115, wherein a first dose is administered, wherein a second dose is administered 24-34 days after the first dose, and wherein a third dose is administered 85 days after the first dose.

Embodiment 155

The method of any of embodiments 113-115, wherein a first dose is administered, wherein a second dose is administered 15 days after the first dose, and wherein a third dose is administered 85 days after the first dose.

Embodiment 156

The method of any of embodiments 113-115, wherein a first dose is administered, wherein a second dose is administered 15 days after the first dose, and wherein a third dose is administered 85 days after the first dose.

Embodiment 157

The method of any of embodiments 113-115, wherein a first dose is administered, wherein a second dose is administered 13-16 days after the first dose, and wherein a third dose is administered 208 to 215 days after the first dose.

Embodiment 158

The method of any of embodiments 113-115, wherein a first dose is administered, wherein a second dose is administered 15 days after the first dose, and wherein a third dose is administered 208 to 215 days after the first dose.

Embodiment 159

The method of any of embodiments 113-115, wherein a first dose is administered, wherein a second dose is administered 15 days after the first dose, and wherein a third dose is administered 211 days after the first dose.

Embodiment 160

The method of any of embodiments 1-159, comprising co-administration of the antisense compound and at least one other therapy.

Embodiment 161

The method of embodiment 160, wherein antisense compound and at least one other therapy are co-administered at the same time.

Embodiment 162

The method of embodiment 160, wherein the antisense compound is administered prior to administration of the at least one other therapy.

Embodiment 163

The method of embodiment 160, wherein the antisense compound is administered after administration of the at least one other therapy.

Embodiment 164

The method of any of embodiments 160-163 wherein the at least one other therapy comprises administration of one or more of valproic acid, riluzole, hydroxyurea, and a butyrate.

Embodiment 165

The method of any of embodiments 160-163 wherein at least one other therapy comprises administration of trichostatin-A.

Embodiment 166

The method of any of embodiments 160-163 wherein the at least one other therapy comprises administration of stem cells.

Embodiment 167

The method of any of embodiments 160-163 wherein at least one other therapy comprises administration of Insulin-like Growth Factor-1.

Embodiment 168

The method of any of embodiments 160-163 wherein at least one other therapy is gene therapy.

Embodiment 169

The method of any of embodiments 1-168, wherein the subject has type I SMA

Embodiment 170

The method of any of embodiments 1-168, wherein the subject has type II SMA.

Embodiment 171

The method of any of embodiments 1-168, embodiments wherein the subject has type III SMA.

Embodiment 172

The method of any of embodiments 1-171, wherein a first dose is administered in utero.

Embodiment 173

The method of any of embodiments 1-171, wherein a first dose is administered within 1 week of birth of the subject.

Embodiment 174

The method of any of embodiments 1-171, wherein a first dose is administered within 1 month of birth of the subject.

Embodiment 175

The method of any of embodiments 1-171, wherein a first dose is administered within 3 months of birth of the subject.

Embodiment 176

The method of any of embodiments 1-171, wherein a first dose is administered within 6 months of birth of the subject.

Embodiment 177

The method of any of embodiments 1-171, wherein a first dose is administered when the subject is from 1 to 2 years of age.

Embodiment 178

The method of any of embodiments 1-171, wherein a first dose is administered when the subject is from 1 to 15 years of age.

Embodiment 179

The method of any of embodiments 1-171, wherein a first dose is administered when the subject is older than 15 years of age.

Embodiment 180

The method of any of embodiments 1-179, comprising identifying a subject having SMA.

Embodiment 181

The method of embodiment 180, wherein the subject is identified by measuring electrical activity of one or more muscles of the subject.

Embodiment 182

The method of embodiment 180, wherein the subject is identified by a genetic test to determine whether the subject has a mutation in the subject's SMN1 gene.

Embodiment 183

The method of embodiment 180, wherein the subject is identified by muscle biopsy.

Embodiment 184

The method of any of embodiments 1-183, wherein the ameliorating at least one symptom of spinal muscular atrophy comprises improved motor function in the subject.

Embodiment 185

The method of any of embodiments 1-184, wherein the ameliorating at least one symptom of spinal muscular atrophy comprises delayed or reduced loss of motor function in the subject.

Embodiment 186

The method of any of embodiments 1-184, wherein the ameliorating at least one symptom of spinal muscular atrophy comprises improved respiratory function.

Embodiment 187

The method of any of embodiments 1-184, wherein the ameliorating at least one symptom of spinal muscular atrophy comprises improved survival.

Embodiment 188

The method of any of embodiments 1-184, wherein the ameliorating at least one symptom of spinal muscular atrophy comprises stable CMAP.

Embodiment 189

The method of any of embodiments 1-184, wherein the ameliorating at least one symptom of spinal muscular

Embodiment 190

The method of embodiment 189, wherein the patient demonstrates an increase in a patient's Hammersmith Motor Function Scale-Expanded greater than 3 points.

Embodiment 191

The method of embodiment 189, wherein the patient demonstrates an increase in a patient's Hammersmith Motor Function Scale-Expanded greater than 4 points.

Embodiment 192

The method of embodiment 189, wherein the patient demonstrates an increase in a patient's Hammersmith Motor Function Scale-Expanded greater than 5 points.

Embodiment 193

The method of embodiment 189, wherein the patient demonstrates an increase in a patient's Hammersmith Motor Function Scale-Expanded greater than 6 points.

Embodiment 194

The method of embodiment 189, wherein the patient demonstrates an increase in a patient's Hammersmith Motor Function Scale-Expanded greater than 7 points.

Embodiment 195

The method of embodiment 189, wherein the patient demonstrates an increase in a patient's Hammersmith Motor Function Scale-Expanded greater than 8 points.

Embodiment 196

The method of any of embodiments 189 to 195, wherein the increase a patient's Hammersmith Motor Function Scale-Expanded occurs 85 days after first dose.

Embodiment 197

The method of any of embodiments 189 to 195, wherein the increase a patient's Hammersmith Motor Function Scale-Expanded improves up to 85 days after first dose.

Embodiment 198

The method of any of embodiments 189 to 195, wherein the increase a patient's Hammersmith Motor Function Scale-Expanded occurs 9, 10, 11, 12, or 13 months after first dose.

Embodiment 199

The method of any of embodiments 189 to 195, wherein the increase a patient's Hammersmith Motor Function Scale-Expanded improves up to 9, 10, 11, 12, or 13 months after first dose.

Embodiment 200

The method of any of embodiments 189 to 195, wherein the increase a patient's Hammersmith Motor Function Scale-Expanded occurs 14 months after first dose.

Embodiment 201

The method of any of embodiments 189 to 195, wherein the increase a patient's Hammersmith Motor Function Scale-Expanded improves up to 14 months after first dose.

Embodiment 202

The method of any of embodiments 1-202, wherein ameliorating at least one symptom of spinal muscular atrophy comprises a stable Hammersmith Motor Function Scale-Expanded.

Embodiment 203

The method of any of embodiments 1-202, wherein the ameliorating at least one symptom of spinal muscular atrophy comprises an increase in a patient's MUNE.

Embodiment 204

The method of embodiment 203, wherein the patient demonstrates an increase in a patient's MUNE of at least 5.

Embodiment 205

The method of embodiment 203, wherein the patient demonstrates an increase in a patient's MUNE of at least 8.

Embodiment 206

The method of embodiment 203, wherein the patient demonstrates an increase in a patient's MUNE of at least 10.

Embodiment 207

The method of embodiment 203, wherein the patient demonstrates an increase in a patient's MUNE of at least 12.

Embodiment 208

The method of embodiment 203, wherein the patient demonstrates an increase in a patient's MUNE of at least 14.

Embodiment 209

The method of embodiment 203, wherein the patient demonstrates an increase in a patient's MUNE of at least 20.

Embodiment 210

The method of any of embodiments 1-209, wherein at least one nucleoside of the antisense oligonucleotide comprises a modified sugar moiety.

Embodiment 211

The method of embodiment 210, wherein the at least one modified sugar moiety comprises a 2'-methoxyethyl sugar moiety.

Embodiment 212

The method of any of embodiments 1-211, wherein essentially each nucleoside of the antisense oligonucleotide comprises a modified sugar moiety.

Embodiment 213

The method of embodiment 212, wherein the nucleosides comprising a modified sugar moiety all comprise the same sugar modification.

Embodiment 214

The method of embodiment 213, wherein each modified sugar moiety comprises a 2'-methoxyethyl sugar moiety.

Embodiment 215

The method of any of embodiments 1-214, wherein each nucleoside of the antisense oligonucleotide comprises a modified sugar moiety.

Embodiment 216

The method of embodiment 215, wherein the nucleosides all comprise the same sugar modification.

Embodiment 217

The method of embodiment 216, wherein each modified sugar moiety comprises a 2'-methoxyethyl sugar moiety.

Embodiment 218

The method of any of embodiments 1-217, wherein at least one internucleoside linkage is a phosphorothioate internucleoside linkage.

Embodiment 219

The method of embodiment 218, wherein each internucleoside linkage is a phosphorothioate internucleoside linkage.

Embodiment 220

The method of any of embodiments 1-219, wherein the antisense oligonucleotide consists of 10 to 25 linked nucleosides.

Embodiment 221

The method of any of embodiments 1-220, wherein the antisense oligonucleotide consists of 12 to 22 linked nucleosides.

Embodiment 222

The method of any of embodiments 1-220, wherein the antisense oligonucleotide consists of 15 to 20 linked nucleosides.

Embodiment 223

The method of any of embodiments 1-220, wherein the antisense oligonucleotide consists of 18 linked nucleosides.

Embodiment 224

The method of any of embodiments 1-223, wherein the antisense oligonucleotide is at least 90% complementary to the nucleic acid encoding human SMN2.

Embodiment 225

The method of embodiment 224, wherein the antisense oligonucleotide is fully complementary to the nucleic acid encoding human SMN2.

Embodiment 226

The method of any of embodiments 1-225, wherein the oligonucleotide has a nucleobase sequence comprising at least 10 contiguous nucleobases of the nucleobase sequence SEQ ID NO: 1.

Embodiment 227

The method of embodiment 226, wherein the oligonucleotide has a nucleobase sequence comprising at least 15 contiguous nucleobases of the nucleobase sequence SEQ ID NO: 1.

Embodiment 228

The method of embodiment 227, wherein the oligonucleotide has a nucleobase sequence comprising the nucleobase sequence SEQ ID NO: 1.

Embodiment 229

The method of embodiment 226, wherein the oligonucleotide has a nucleobase sequence consisting of the nucleobase sequence SEQ ID NO: 1.

Embodiment 230

The method of any of embodiments 1-229, wherein the antisense compound comprises a conjugate group or terminal group.

Embodiment 231

The method of any of embodiments 1-230, wherein the antisense compound consists of the antisense oligonucleotide.

Embodiment 232

The method of any of embodiments 1-231, wherein the antisense compound is administered into the cerebrospinal fluid and is also administered systemically.

Embodiment 233

The method of embodiment 232, wherein the systemic administration is by intravenous or intraperitoneal injection.

Embodiment 234

The method of embodiment 232 or 233, wherein the systemic administration and the administration into the central nervous system are performed at the same time.

Embodiment 235

The method of embodiment 232 or 233, wherein the systemic administration and the administration into the central nervous system are performed at different times.

Embodiment 236

An antisense compound comprising an antisense oligonucleotide complementary to intron 7 of a nucleic acid encoding human SMN2, for use in a method according to any of embodiments 1-235.

Embodiment 237

The antisense compound according to embodiment 236, for use in treating a disease or condition associated with survival motor neuron 1 (SMN1).

Embodiment 238

Use of an antisense compound comprising an antisense oligonucleotide complementary to intron 7 of a nucleic acid encoding human SMN2 in the manufacture of a medicament for use in a method according to any preceding embodiment.

Embodiment 239

The use according to embodiment 238, wherein the medicament is for treating a disease or condition associated with survival motor neuron 1 (SMN1).

Embodiment 240

Use of an antisense compound comprising an antisense oligonucleotide complementary to intron 7 of a nucleic acid encoding human SMN2 in the manufacture of a medicament for use in a method according to any of embodiments 1 to 237.

BRIEF DESCRIPTION OF THE FIGURES

FIG. 1 shows the change in the Hammersmith Motor Function Scale Expanded observed at 29 or 85 days for patients dosed with 1 mg, 3 mg, 6 mg, or 9 mg of ISIS 396443.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

I. DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

"Nucleoside" means a compound comprising a heterocyclic base moiety and a sugar moiety. Nucleosides include, but are not limited to, naturally occurring nucleosides, modified nucleosides, and nucleosides having mimetic bases and/or sugar groups. Nucleosides may be modified with any of a variety of substituents.

"Sugar moiety" means a natural or modified sugar or sugar surrogate.

"Natural sugar" means a ribofuranose moiety of DNA (2'-H) or RNA (2'-OH).

"Modified sugar" means a ribofuranose moiety comprising at least one substituent other than that of a natural sugar.

"Sugar surrogate" means a structure other than a ribofuranose ring which is capable of substituting for the sugar of a nucleoside. Examples of sugar surrogates include, but are not limited to, open ring systems, 6-membered rings, sugars in which the oxygen is replace with, for example, sulfur or nitrogen. For example, sugar surrogates include, but are not limited to morpholinos and 4'-thio-containing sugars.

"Nucleobase" means the heterocyclic base portion of a nucleoside. Nucleobases may be naturally occurring or may be modified. In certain embodiments, a nucleobase may comprise any atom or group of atoms capable of hydrogen bonding to a nucleobase of another nucleic acid.

"Nucleotide" means a nucleoside comprising a phosphate linking group. As used herein, nucleosides include nucleotides.

"Modified nucleoside" a nucleoside comprising at least one modification compared to naturally occurring RNA or DNA nucleosides. Such modification may be at the sugar moiety and/or at the nucleobase.

"Bicyclic nucleoside" or "BNA" means a nucleoside wherein the sugar moiety of the nucleoside comprises a bridge connecting two carbon atoms of the sugar ring, thereby forming a bicyclic sugar moiety.

"4'-2' bicyclic nucleoside" means a bicyclic nucleoside comprising a furanose ring comprising a bridge connecting two carbon atoms of the furanose ring connects the 2' carbon atom and the 4' carbon atom of the sugar ring.

"2'-modified" or "2'-substituted" means a nucleoside comprising a sugar comprising a substituent at the 2' position other than H or OH.

"2'-OMe" or "2'-OCH$_3$" or "2'-O-methyl" each means a nucleoside comprising a sugar comprising an —OCH$_3$ group at the 2' position of the sugar ring.

"MOE" or "2'-MOE" or "2'-OCH$_2$CH$_2$OCH$_3$" or "2'-O-methoxyethyl" each means a nucleoside comprising a sugar comprising a —OCH$_2$CH$_2$OCH$_3$ group at the 2' position of the sugar ring.

"Oligonucleotide" means a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

"Oligonucleoside" means an oligonucleotide in which none of the internucleoside linkages contains a phosphorus atom. As used herein, oligonucleotides include oligonucleosides.

"Modified oligonucleotide" means an oligonucleotide comprising at least one modified nucleoside and/or at least one modified internucleoside linkage.

"Internucleoside linkage" means a covalent linkage between adjacent nucleosides of an oligonucleotide.

"Naturally occurring internucleoside linkage" means a 3' to 5' phosphodiester linkage.

"Modified internucleoside linkage" means any internucleoside linkage other than a naturally occurring internucleoside linkage.

"Oligomeric compound" means a compound comprising an oligonucleotide. In certain embodiments, an oligomeric compound consists of an oligonucleotide. In certain embodiments, an oligomeric compound further comprises one or more conjugate and/or terminal groups.

"Antisense compound" means an oligomeric compound, at least a portion of which is at least partially complementary to a target nucleic acid to which it hybridizes, wherein such hybridization results at least one antisense activity.

"Antisense oligonucleotide" means an antisense compound wherein the oligomeric compound consists of an oligonucleotide.

"Antisense activity" refers to any detectable and/or measurable effect attributable to the hybridization of an antisense compound to its target nucleic acid. In certain embodiments, such antisense activity is an increase or decrease in an amount of a nucleic acid or protein. In certain embodiments, such antisense activity is a change in the ratio of splice variants of a nucleic acid or protein. In certain embodiments, such antisense activity is a phenotypic change in a cell and/or subject.

"Detecting" or "measuring" of antisense activity may be direct or indirect. For example, in certain embodiments, antisense activity is assessed by detecting and/or measuring the amount of target nucleic acid or protein or the relative amounts of splice variants of a target nucleic acid or protein. In certain embodiments, antisense activity is detected by observing a phenotypic change in a cell or animal. In connection with any activity, response, or effect, the terms "detecting" and "measuring," indicate that a test for detecting or measuring is performed. Such detection and/or measuring may include values of zero. Thus, if a test for detection or measuring results in a finding of no activity (activity of zero), the step of detecting or measuring the activity has nevertheless been performed.

"Target nucleic acid" refers to any nucleic acid molecule the expression, amount, or activity of which is capable of being modulated by an antisense compound.

"Target mRNA" means a pre-selected RNA molecule that encodes a protein.

"Target pre-mRNA" means a pre-selected RNA transcript that has not been fully processed into mRNA. Notably, pre-mRNA includes one or more intron.

"Target protein" means a protein encoded by a target nucleic acid.

"Modulation" means to a perturbation of function or activity. In certain embodiments, modulation means an increase in gene expression. In certain embodiments, modulation means a decrease in gene expression.

"Expression" means any functions and steps by which a gene's coded information is converted into structures present and operating in a cell.

"Nucleobase sequence" means the order of contiguous nucleobases, in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that a first nucleic acid is capable of hybridizing to a second nucleic acid under stringent hybridization conditions. For example, an antisense compound is complementary to its target nucleic acid if it is capable of hybridizing to the target nucleic acid under stringent hybridization conditions.

"Fully complementary" means each nucleobase of a first nucleic acid is capable of pairing with a nucleobase at each corresponding contiguous position in a second nucleic acid.

"Percent complementarity" of an antisense compound means the percentage of nucleobases of the antisense compound that are complementary to an equal-length portion of a target nucleic acid. Percent complementarity is calculated by dividing the number of nucleobases of the antisense oligonucleotide that are complementary to nucleobases at corresponding contiguous positions in the target nucleic acid by the total length of the antisense compound.

"Percent identity" means the number of nucleobases in first nucleic acid that are identical to nucleobases at corresponding positions in a second nucleic acid, divided by the total number of nucleobases in the first nucleic acid.

"Hybridize" means the annealing of complementary nucleic acids that occurs through nucleobase complementarity.

"Mismatch" means a nucleobase of a first nucleic acid that is not capable of pairing with a nucleobase at a corresponding position of a second nucleic acid.

"Identical nucleobase sequence" means having the same nucleobase sequence, independent of any chemical modifications to the nucleosides.

"Different modifications" or "differently modified" refer to nucleosides or internucleoside linkages that have different nucleoside modifications or internucleoside linkages than one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified, unless otherwise indicated. For example, a nucleoside comprising a 2'-OMe modified sugar and an adenine nucleobase and a nucleoside comprising a 2'-OMe modified sugar and a thymine nucleobase are not differently modified.

"The same modifications" refer to nucleosides and internucleoside linkages (including unmodified nucleosides and internucleoside linkages) that are the same as one another. Thus, for example, two unmodified DNA nucleoside have "the same modification," even though the DNA nucleoside is unmodified.

"Type of modification" or nucleoside of a "type" means the modification of a nucleoside and includes modified and unmodified nucleosides. Accordingly, unless otherwise indicated, a "nucleoside having a modification of a first type" may be an unmodified nucleoside.

"Separate regions" of an oligonucleotide means a portion of an oligonucleotide wherein the nucleosides and internucleoside linkages within the region all comprise the same modifications; and the nucleosides and/or the internucleoside linkages of any neighboring portions include at least one different modification.

"Motif" means a pattern of modified and/or unmodified nucleobases, sugars, and/or internucleoside linkages in an oligonucleotide.

"Fully modified oligonucleotide" means each nucleobase, each sugar, and/or each internucleoside linkage is modified.

"Uniformly modified oligonucleotide" means each nucleobase, each sugar, and/or each internucleoside linkage has the same modification throughout the modified oligonucleotide.

"Alternating motif" means an oligonucleotide or a portion thereof, having at least four separate regions of modified nucleosides in a pattern $(AB)_nA_m$ where A represents a region of nucleosides having a first type of modification; B represent a region of nucleosides having a different type of modification; n is 2-15; and m is 0 or 1. Thus, in certain embodiments, alternating motifs include 4, 5, 6, 7, 8, 9, 10, 11, 12, 13, 14, 15, 16, 17, 18, 19, or 20 or more alternating regions. In certain embodiments, each A region and each B region independently comprises 1-4 nucleosides.

"Subject" means a human or non-human animal selected for treatment or therapy.

"Subject in need thereof" means a subject identified as in need of a therapy or treatment. In such embodiments, a subject has one or more indications of having or developing SMA.

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, or intramuscular administration.

"Systemic administration" means administration to an area other than the intended locus of activity. Examples or systemic administration are subcutaneous administration and intravenous administration, and intraperitoneal administration.

"Subcutaneous administration" means administration just below the skin.

"Intravenous administration" means administration into a vein.

"Cerebrospinal fluid" or "CSF" means the fluid filling the space around the brain and spinal cord.

"Administration into the cerebrospinal fluid" means any administration that delivers a substance directly into the CSF.

"Intracerebroventricular" or "ICV" mean administration into the ventricular system of the brain.

"Intrathecal" or "IT" means administration into the CSF under the arachnoid membrane which covers the brain and spinal cord. IT injection is performed through the theca of the spinal cord into the subarachnoid space, where a pharmaceutical agent is injected into the sheath surrounding the spinal cord.

"Induction phase" means a dosing phase during which administration is initiated and steady state concentrations of active pharmaceutical agent are achieved in a target tissue. For example, an induction phase is a dosing phase during which steady state concentrations of antisense oligonucleotide are achieved in liver.

"Maintenance phase" means a dosing phase after target tissue steady state concentrations of drug have been achieved.

"Duration" means the period of time during which an activity or event continues. For example, the duration of an induction phase is the period of time during which induction doses are administered.

"Maintenance dose" means a dose administered at a single administration during the maintenance phase. As used herein, "induction dose" means a dose administered at a single administration during the induction phase.

"Co-administration" means administration of two or more pharmaceutical agents to a subject. The two or more pharmaceutical agents may be in a single pharmaceutical composition, or may be in separate pharmaceutical compositions. Each of the two or more pharmaceutical agents may be administered through the same or different routes of administration. Co-administration encompasses administration in parallel or sequentially.

"Therapy" means a disease treatment method. In certain embodiments, therapy includes, but is not limited to surgical therapies, chemical therapies, and physical interventions, such as assisted respiration, feeding tubes, and physical therapy for the purpose of increasing strength.

"Treatment" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Prevent the onset of" means to prevent the development a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition.

"Slow the progression of" means that the severity of at least one symptom associated with a disease or condition worsens less quickly.

"Exon 7 amino acids" means the portion of an SMN protein that correspond to exon 7 of the SMN RNA. Exon 7 amino acids are present in SMN protein expressed from SMN RNA where exon 7 was not excluded during splicing.

"SMN protein" means normal full length survival motor neuron protein. SMN may be expressed from either an SMN1 gene or from an SMN2 gene, provided that exon 7 is present in the mature mRNA and the exon 7 amino acids are present in the SMN protein.

"Dose" means a specified quantity of a pharmaceutical agent provided in a single administration or over a specified amount of time. In certain embodiments, a dose may be administered in two or more boluses, tablets, or injections. For example, in certain embodiments, where subcutaneous or intrathecal or ICV administration is desired, the desired dose requires a volume not easily accommodated by a single injection. In such embodiments, two or more injections may be used to achieve the desired dose. In the setting of continuous infusion, dose may be expressed as the quantity of a pharmaceutical agent delivered per unit of time.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Equivalent dose" means a dose amount that is used to calculate an adjusted dose, wherein the adjusted dose is based on the CSF volume, dose concentration, or any other criteria known to one having skill in the art. For example, in certain embodiments it may be desirable to administer an equivalent dose of 12 mg of ISIS 396443 to a patient having one or more symptoms of SMA, however based on the patient's age and estimated CSF volume the actual dose of ISIS 396443 may be adjusted to an amount less than 12 mg. For example, it may be desirable to administer an equivalent dose of 12 mg of ISIS 396443 to an SMA patient between 0 and 3 months of age, however based on the patient's age and estimated CSF volume, the actual adjusted dose of ISIS 396443 received by the SMA patient would be 9.6 mg. In certain embodiments, adjusted doses may be calculated based on a desired equivalent dose by using CSF volume scaling as described in Matsuzawa J, Matsui M, Konishi T, Noguchi K, Gur R C, Bilker W, Miyawaki T. Age-related volumetric changes of brain gray and white matter in healthy infants and children. Cereb Cortex 2001 April; 11(4):335-342, which is hereby incorporated by reference in its entirety).

"Adjusted dose" means a dose that is adjusted from a dose or equivalent dose. In certain embodiments and adjusted dose is based on one or more criteria known to those having skill in the art. In certain embodiments the adjusted dose is based on the patient's age, weight, or estimated CSF volume. In certain embodiments, an adjusted dose is derived from an equivalent dose. In certain embodiments, adjusted doses may be calculated based on a desired equivalent dose by using CSF volume scaling as described in Matsuzawa J, Matsui M, Konishi T, Noguchi K, Gur R C, Bilker W, Miyawaki T. Age-related volumetric changes of brain gray and white matter in healthy infants and children. Cereb Cortex 2001 April; 11(4):335-342, which is hereby incorporated by reference in its entirety).

"Therapeutically effective amount" means an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a modified oligonucleotide and a sterile aqueous solution.

"Acceptable safety profile" means a pattern of side effects that is within clinically acceptable limits.

"Side effect" means a physiological response attributable to a treatment other than desired effects.

1. Certain Modified Oligonucleotides

In certain embodiments, the present invention provides methods and compositions involving antisense oligonucleotides comprising one or more modification compared to oligonucleotides of naturally occurring oligomers, such as DNA or RNA. Such modified antisense oligonucleotides may possess one or more desirable properties. Certain such modifications alter the antisense activity of the antisense oligonucleotide, for example by increasing affinity of the antisense oligonucleotide for its target nucleic acid, increasing its resistance to one or more nucleases, and/or altering the pharmacokinetics or tissue distribution of the oligonucleotide. In certain embodiments, such modified antisense oligonucleotides comprise one or more modified nucleosides and/or one or more modified nucleoside linkages and/or one or more conjugate groups.

a. Certain Modified Nucleosides

In certain embodiments, antisense oligonucleotides comprise one or more modified nucleosides. Such modified nucleosides may include a modified sugar and/or a modified nucleobase. In certain embodiments, incorporation of such modified nucleosides in an oligonucleotide results in increased affinity for a target nucleic acid and/or increased stability, including but not limited to, increased resistance to nuclease degradation, and or improved toxicity and/or uptake properties of the modified oligonucleotide.

i. Certain Nucleobases

The naturally occurring base portion of nucleosides are heterocyclic base, typically purines and pyrimidines. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to incorporation into the compounds described herein. In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

ii. Certain Modified Sugars and Sugar Surrogates

Antisense oligonucleotides of the present invention can optionally contain one or more nucleosides wherein the sugar moiety is modified, compared to a natural sugar. Oligonucleotides comprising such sugar modified nucleosides may have enhanced nuclease stability, increased binding affinity or some other beneficial biological property. Such modifications include without limitation, addition of substituent groups, bridging of non-geminal ring atoms to form a bicyclic nucleic acid (BNA), replacement of the ribosyl ring oxygen atom with S, N(R), or $C(R_1)(R)_2$ (R=H, $C_1$-$C_{12}$ alkyl or a protecting group) and combinations of these such as for example a 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$ and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, O(CH$_2$)$_2$SCH$_3$, O(CH$_2$)$_2$—O—N(R$_m$)(R$_n$), and O—CH$_2$—C(=O)—N(R$_m$)(R$_n$), where each R$_m$ and R$_n$ is, independently, H or substituted or unsubstituted C$_1$-C$_{10}$ alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-β-D-(CH$_2$)—O-2' (β-D-LNA); 4'-(CH$_2$)—S-2; 4'-α-L-(CH$_2$)—O-2' (α-L-LNA); 4'-(CH$_2$)$_2$—O-2' (ENA); 4'-C(CH$_3$)$_2$—O-2' (see PCT/US2008/068922); 4'-CH(CH$_3$)—O-2' and 4'-C—H(CH$_2$OCH$_3$)—O-2' (see U.S. Pat. No. 7,399,845, issued on Jul. 15, 2008); 4'-CH$_2$—N(OCH$_3$)-2' (see PCT/US2008/064591); 4'-CH$_2$—O—N(CH$_3$)-2' (see published U.S. Patent Application US2004-0171570, published Sep. 2, 2004); 4'-CH$_2$—N(R)—O-2' (see U.S. Pat. No. 7,427,672, issued on Sep. 23, 2008); 4'-CH$_2$—C(CH$_3$)-2' and 4'-CH$_2$—C(=CH$_2$)-2' (see PCT/US2008/066154); and wherein R is, independently, H, C$_1$-C$_{12}$ alkyl, or a protecting group.

In certain embodiments, the present invention provides modified nucleosides comprising modified sugar moieties that are not bicyclic sugar moieties. Certain such modified nucleosides are known. In certain embodiments, the sugar ring of a nucleoside may be modified at any position. Examples of sugar modifications useful in this invention include, but are not limited to compounds comprising a sugar substituent group selected from: OH, F, O-alkyl, S-alkyl, N-alkyl, or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. In certain such embodiments, such substituents are at the 2' position of the sugar.

In certain embodiments, modified nucleosides comprise a substituent at the 2' position of the sugar. In certain embodiments, such substituents are selected from among: a halide (including, but not limited to F), allyl, amino, azido, thio, O-allyl, O—C$_1$-C$_{10}$ alkyl, —OCF$_3$, O—(CH$_2$)$_2$—O—CH$_3$, 2'-O(CH$_2$)$_2$SCH$_3$, O—(CH$_2$)$_2$—O—N(R$_m$)(R$_n$), or O—CH2-C(=O)—N(R$_m$)(R$_n$), where each R$_m$ and R$_n$ is, independently, H or substituted or unsubstituted C$_1$-C$_{10}$ alkyl.

In certain embodiments, modified nucleosides suitable for use in the present invention are: 2-methoxyethoxy, 2'-O-methyl (2'-O—CH$_3$), 2'-fluoro (2'-F).

In certain embodiments, modified nucleosides having a substituent group at the 2'-position selected from: O[(CH$_2$)$_n$O]$_m$CH$_3$, O(CH$_2$)$_n$NH$_2$, O(CH$_2$)$_n$CH$_3$, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-sugar substituent groups include: C$_1$ to C$_{10}$ alkyl, substituted alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an oligomeric compound, and other substituents having similar properties.

In certain embodiments, modified nucleosides comprise a 2'-MOE side chain (Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

In certain embodiments, 2'-sugar substituent groups are in either the arabino (up) position or ribo (down) position. In certain such embodiments, a 2'-arabino modification is 2'-F arabino (FANA). Similar modifications can also be made at other positions on the sugar, particularly the 3' position of the sugar on a 3' terminal nucleoside or in 2'-5' linked oligonucleotides and the 5' position of 5' terminal nucleotide.

In certain embodiments, nucleosides suitable for use in the present invention have sugar surrogates such as cyclobutyl in place of the ribofuranosyl sugar. Representative U.S. patents that teach the preparation of such modified sugar structures include, but are not limited to, U.S.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

In certain embodiments, the present invention provides nucleosides comprising a modification at the 2'-position of the sugar. In certain embodiments, the invention provides nucleosides comprising a modification at the 5'-position of the sugar. In certain embodiments, the invention provides nucleosides comprising modifications at the 2'-position and the 5'-position of the sugar. In certain embodiments, modified nucleosides may be useful for incorporation into oligonucleotides. In certain embodiment, modified nucleosides are incorporated into oligonucleosides at the 5'-end of the oligonucleotide.

b. Certain Internucleoside Linkages

Antisense oligonucleotides of the present invention can optionally contain one or more modified internucleoside linkages. The two main classes of linking groups are defined by the presence or absence of a phosphorus atom. Representative phosphorus containing linkages include, but are not limited to, phosphodiesters (P=O), phosphotriesters, methylphosphonates, phosphoramidate, and phosphorothioates (P=S). Representative non-phosphorus containing linking groups include, but are not limited to, methylenemethylimino (—CH2-N(CH3)-O—CH2-), thiodiester (—O—C(O)—S—), thionocarbamate (—O—C(O)(NH)—S—); siloxane (—O—Si(H)2-O—); and N,N'-dimethylhydrazine (—CH2-N(CH3)-N(CH3)-). Oligonucleotides having non-phosphorus linking groups are referred to as oligonucleosides. Modified linkages, compared to natural phosphodiester linkages, can be used to alter, typically increase, nuclease resistance of the oligonucleotides. In certain embodiments, linkages having a chiral atom can be prepared as racemic mixtures, as separate enantiomers. Representative chiral linkages include, but are not limited to, alkylphosphonates and phosphorothioates. Methods of preparation of phosphorous-containing and non-phosphorous-containing linkages are well known to those skilled in the art.

The antisense oligonucleotides described herein contain one or more asymmetric centers and thus give rise to enantiomers, diastereomers, and other stereoisomeric configurations that may be defined, in terms of absolute stereochemistry, as (R) or (S), such as for sugar anomers, or as (D) or (L) such as for amino acids et al. Included in the antisense compounds provided herein are all such possible isomers, as well as their racemic and optically pure forms.

In certain embodiments, antisense oligonucleotides have at least one modified internucleoside linkage. In certain embodiments, antisense oligonucleotides have at least 2 modified internucleoside linkages. In certain embodiments, antisense oligonucleotides have at least 3 modified internucleoside linkages. In certain embodiments, antisense oligonucleotides have at least 10 modified internucleoside linkages. In certain embodiments, each internucleoside linkage of an antisense oligonucleotide is a modified internucleoside linkage. In certain embodiments, such modified internucleoside linkages are phosphorothioate linkages.

c. Lengths

In certain embodiments, the present invention provides antisense oligonucleotides of any of a variety of ranges of lengths. In certain embodiments, the invention provides antisense compounds or antisense oligonucleotides comprising or consisting of X-Y linked nucleosides, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides antisense compounds or antisense oligonucleotides comprising or consisting of: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked nucleosides.

In certain embodiments, antisense compounds or antisense oligonucleotides of the present invention are 15 nucleosides in length. In certain embodiments, antisense compounds or antisense oligonucleotides of the present invention are 16 nucleosides in length. In certain embodiments, antisense compounds or antisense oligonucleotides of the present invention are 17 nucleosides in length. In certain embodiments, antisense compounds or antisense oligonucleotides of the present invention are 18 nucleosides in length. In certain embodiments, antisense compounds or antisense oligonucleotides of the present invention are 19 nucleosides in length. In certain embodiments, antisense compounds or antisense oligonucleotides of the present invention are 20 nucleosides in length.

d. Certain Oligonucleotide Motifs

In certain embodiments, antisense oligonucleotides have chemically modified subunits arranged in specific orientations along their length. In certain embodiments, antisense oligonucleotides of the invention are fully modified. In certain embodiments, antisense oligonucleotides of the invention are uniformly modified. In certain embodiments, antisense oligonucleotides of the invention are uniformly modified and each nucleoside comprises a 2'-MOE sugar moiety. In certain embodiments, antisense oligonucleotides of the invention are uniformly modified and each nucleoside comprises a 2'-OMe sugar moiety. In certain embodiments, antisense oligonucleotides of the invention are uniformly modified and each nucleoside comprises a morpholino sugar moiety.

In certain embodiments, oligonucleotides of the invention comprise an alternating motif. In certain such embodiments, the alternating modification types are selected from among 2'-MOE, 2'-F, a bicyclic sugar-modified nucleoside, and DNA (unmodified 2'-deoxy). In certain such embodiments, each alternating region comprises a single nucleoside.

In certain embodiments, oligonucleotides of the invention comprise one or more block of nucleosides of a first type and one or more block of nucleosides of a second type.

In certain embodiments, one or more alternating regions in an alternating motif include more than a single nucleoside of a type. For example, oligomeric compounds of the present invention may include one or more regions of any of the following nucleoside motifs:

$Nu_1 Nu_1 Nu_2 Nu_2 Nu_1 Nu_1$;

$Nu_1 Nu_2 Nu_2 Nu_1 Nu_2 Nu_2$;

$Nu_1 Nu_1 Nu_2 Nu_1 Nu_1 Nu_2$;

$Nu_1 Nu_2 Nu_2 Nu_1 Nu_2 Nu_1 Nu_1 Nu_2 Nu_2$;

$Nu_1 Nu_2 Nu_1 Nu_2 Nu_1 Nu_1$;

$Nu_1 Nu_1 Nu_2 Nu_1 Nu_2 Nu_1 Nu_2$;

$Nu_1 Nu_2 Nu_1 Nu_2 Nu_1 Nu_1$;

$Nu_1 Nu_2 Nu_2 Nu_1 Nu_1 Nu_2 Nu_2 Nu_1 Nu_2 Nu_1 Nu_2 Nu_1 Nu_1$;

$Nu_2 Nu_1 Nu_2 Nu_2 Nu_1 Nu_1 Nu_2 Nu_2 Nu_1 Nu_2 Nu_1 Nu_2 Nu_1$; or $Nu_1 Nu_2 Nu_1 Nu_2 Nu_2 Nu_1 Nu_1 Nu_2 Nu_2 Nu_1 Nu_2 Nu_1 Nu_2 Nu_1 Nu_1$;

wherein $Nu_1$ is a nucleoside of a first type and $Nu_2$ is a nucleoside of a second type. In certain embodiments, one of $Nu_1$ and $Nu_2$ is a 2'-MOE nucleoside and the other of $Nu_1$ and $Nu_2$ is a selected from: a 2'-OMe modified nucleoside, BNA, and an unmodified DNA or RNA nucleoside.

2. Oligomeric Compounds

In certain embodiments, the present invention provides oligomeric compounds. In certain embodiments, oligomeric compounds are comprised only of an oligonucleotide. In certain embodiments, an oligomeric compound comprises an oligonucleotide and one or more conjugate and/or terminal group. Such conjugate and/or terminal groups may be added to oligonucleotides having any of the chemical motifs discussed above. Thus, for example, an oligomeric compound comprising an oligonucleotide having region of alternating nucleosides may comprise a terminal group.

a. Certain Conjugate Groups

In certain embodiments, oligonucleotides of the present invention are modified by attachment of one or more conjugate groups. In general, conjugate groups modify one or more properties of the attached oligomeric compound including but not limited to, pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130.

Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Conjugate groups may be attached to either or both ends of an oligonucleotide (terminal conjugate groups) and/or at any internal position.

b. Terminal Groups

In certain embodiments, oligomeric compounds comprise terminal groups at one or both ends. In certain embodiments, a terminal group may comprise any of the conjugate groups discussed above. In certain embodiments, terminal groups may comprise additional nucleosides and/or inverted abasic nucleosides. In certain embodiments, a terminal group is a stabilizing group.

In certain embodiments, oligomeric compounds comprise one or more terminal stabilizing group that enhances properties such as for example nuclease stability. Included in stabilizing groups are cap structures. The terms "cap structure" or "terminal cap moiety," as used herein, refer to chemical modifications, which can be attached to one or both of the termini of an oligomeric compound. Certain such terminal modifications protect the oligomeric compounds having terminal nucleic acid moieties from exonuclease degradation, and can help in delivery and/or localization within a cell. The cap can be present at the 5'-terminus (5'-cap) or at the 3'-terminus (3'-cap) or can be present on both termini. (for more details see Wincott et al., International PCT publication No. WO 97/26270; Beaucage and Tyer, 1993, Tetrahedron 49, 1925; U.S. Patent Application Publication No. US 2005/0020525; and WO 03/004602.

In certain embodiments, one or more additional nucleosides is added to one or both terminal ends of an oligonucleotide of an oligomeric compound. Such additional terminal nucleosides are referred to herein as terminal-group nucleosides. In a double-stranded compound, such terminal-group nucleosides are terminal (3' and/or 5') overhangs. In the setting of double-stranded antisense compounds, such terminal-group nucleosides may or may not be complementary to a target nucleic acid. In certain embodiments, the terminal group is a non-nucleoside terminal group. Such non-terminal groups may be any terminal group other than a nucleoside.

3. Antisense

In certain embodiments, oligomeric compounds of the present invention are antisense compounds. Accordingly, in such embodiments, oligomeric compounds hybridize with a target nucleic acid, resulting in an antisense activity.

a. Hybridization

In certain embodiments, the invention provides antisense compounds that specifically hybridize to a target nucleic acid when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

Thus, "stringent hybridization conditions" or "stringent conditions" means conditions under which an antisense compounds hybridize to a target sequence, but to a minimal number of other sequences. Stringent conditions are sequence-dependent and will be different in different circumstances, and "stringent conditions" under which antisense oligonucleotides hybridize to a target sequence are determined by the nature and composition of the antisense oligonucleotides and the assays in which they are being investigated.

It is understood in the art that incorporation of nucleotide affinity modifications may allow for a greater number of mismatches compared to an unmodified compound. Similarly, certain nucleobase sequences may be more tolerant to mismatches than other nucleobase sequences. One of ordinary skill in the art is capable of determining an appropriate number of mismatches between oligonucleotides, or between an antisense oligonucleotide and a target nucleic acid, such as by determining melting temperature (Tm). Tm or ΔTm can be calculated by techniques that are familiar to one of ordinary skill in the art. For example, techniques described in Freier et al. (Nucleic Acids Research, 1997, 25, 22: 4429-4443) allow one of ordinary skill in the art to evaluate nucleotide modifications for their ability to increase the melting temperature of an RNA:DNA duplex.

b. Pre-mRNA Processing

In certain embodiments, antisense compounds provided herein are complementary to a pre-mRNA. In certain embodiments, such antisense compounds alter splicing of the pre-mRNA. In certain such embodiments, the ratio of one variant of a mature mRNA corresponding to a target pre-mRNA to another variant of that mature mRNA is altered. In certain such embodiments, the ratio of one variant of a protein expressed from the target pre-mRNA to another variant of the protein is altered. Certain oligomeric compounds and nucleobase sequences that may be used to alter splicing of a pre-mRNA may be found for example in U.S. Pat. No. 6,210,892; U.S. Pat. No. 5,627,274; U.S. Pat. Nos. 5,665,593; 5,916,808; U.S. Pat. No. 5,976,879; US2006/0172962; US2007/002390; US2005/0074801; US2007/0105807; US2005/0054836; WO 2007/090073; WO2007/047913, Hua et al., PLoS Biol 5(4):e73; Vickers et al., J. Immunol. 2006 Mar. 15; 176(6):3652-61; and Hua et al., American J. of Human Genetics (April 2008) 82, 1-15, each of which is hereby incorporated by reference in its entirety for any purpose. In certain embodiments antisense sequences that alter splicing are modified according to motifs of the present invention.

Antisense is an effective means for modulating the expression of one or more specific gene products and is uniquely useful in a number of therapeutic, diagnostic, and research applications. Provided herein are antisense compounds useful for modulating gene expression via antisense mechanisms of action, including antisense mechanisms based on target occupancy. In one aspect, the antisense compounds provided herein modulate splicing of a target gene. Such modulation includes promoting or inhibiting exon inclusion. Further provided herein are antisense compounds targeted to cis splicing regulatory elements present in pre-mRNA molecules, including exonic splicing enhancers, exonic splicing silencers, intronic splicing enhancers and intronic splicing silencers. Disruption of cis splicing regulatory elements is thought to alter splice site selection, which may lead to an alteration in the composition of splice products.

Processing of eukaryotic pre-mRNAs is a complex process that requires a multitude of signals and protein factors to achieve appropriate mRNA splicing. Exon definition by the spliceosome requires more than the canonical splicing signals which define intron-exon boundaries. One such additional signal is provided by cis-acting regulatory enhancer and silencer sequences. Exonic splicing enhancers (ESE), exonic splicing silencers (ESS), intronic splicing enhancers (ISE) and intron splicing silencers (ISS) have been identified which either repress or enhance usage of splice donor sites or splice acceptor sites, depending on their site and mode of action (Yeo et al. 2004, *Proc. Natl. Acad. Sci. U.S.A.* 101(44):15700-15705). Binding of specific proteins (trans factors) to these regulatory sequences directs the splicing process, either promoting or inhibiting usage of particular splice sites and thus modulating the ratio of splicing products (Scamborova et al. 2004, *Mol. Cell. Biol.* 24(5):1855-1869; Hovhannisyan and Carstens, 2005, *Mol. Cell. Biol.* 25(1):250-263; Minovitsky et al. 2005, *Nucleic Acids Res.* 33(2):714-724).

4. Pharmaceutical Compositions

In certain embodiments, the present invention provides pharmaceutical compositions comprising one or more antisense compound. In certain embodiments, such pharmaceutical composition comprises a sterile saline solution and one or more antisense compound. In certain embodiments, such pharmaceutical composition consists of a sterile saline solution and one or more antisense compound.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments antisense compounds, can be utilized in pharmaceutical compositions by combining such oligomeric compounds with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in certain embodiments, employed in the methods described herein is a pharmaceutical composition comprising an antisense compound and a pharmaceutically acceptable diluent. In certain embodiments, the pharmaceutically acceptable diluent is PBS. In certain embodiments, the pharmaceutically acceptable diluent is artificial CSF.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid-based vectors have been used in nucleic acid therapies in a variety of methods. For example, in one method, the nucleic acid is introduced into preformed liposomes or lipoplexes made of mixtures of cationic lipids and neutral lipids. In another method, DNA complexes with mono- or poly-cationic lipids are formed without the presence of a neutral lipid.

Certain preparations are described in Akinc et al., *Nature Biotechnology* 26, 561-569 (1 May 2008), which is herein incorporated by reference in its entirety.

In certain embodiments, the pharmaceutically acceptable diluent is artificial CSF. In certain embodiments, artificial CSF is commercially available. In certain embodiments, artificial CSF is prepared according to a formulation provided by Harvard Apparatus, Inc. In certain embodiments, each 1 mL of artificial CSF contains the following ingredients:

| Ingredients | Grade | Quantity/ml |
| --- | --- | --- |
| Sodium dihydrogen phosphate dihydrate | USP, Ph. Eur. | 0.050 mg |
| Sodium phosphate dibasic anhydrous | USP, Ph. Eur. | 0.097 mg |
| Sodium chloride | USP, Ph. Eur. | 8.766 mg |
| Potassium chloride | USP, Ph. Eur. | 0.224 mg |
| Calcium chloride dihydrate | USP, Ph. Eur. | 0.206 mg |
| Magnesium chloride hexahydrate | USP, Ph. Eur. | 0.163 mg |
| Sodium hydroxide | NF, Ph. Eur. | As needed |
| Hydrochloric acid | NF, Ph. Eur. | As needed |
| Water for Injection | USP/Ph. Eur. | Q.S. |

In certain embodiments, the artificial CSF formulation vehicle comprises 1 mM phosphate buffer at pH 7.2, adequate sodium chloride to be isotonic, and physiological levels of electrolytes (e.g. potassium, calcium, and magnesium).

5. Administration to a Subject

In certain embodiments, pharmaceutical compositions comprising one or more antisense compound are administered to a subject. In certain embodiments, such pharmaceutical compositions are administered by injection. In certain embodiments, such pharmaceutical compositions are administered by infusion.

In certain embodiments, pharmaceutical compositions are administered by injection or infusion into the CSF. In certain such embodiments, pharmaceutical compositions are administered by direct injection or infusion into the spine. In certain embodiments, pharmaceutical compositions are administered by injection or infusion into the brain. In certain embodiments, pharmaceutical compositions are administered by intrathecal injection or infusion rather than into the spinal cord tissue itself. Without being limited as to theory, in certain embodiments, the antisense compound released into the surrounding CSF and may penetrate into the spinal cord parenchyma. An additional advantage of intrathecal delivery is that the intrathecal route mimics lumbar puncture administration (i.e., spinal tap) already in routine use in humans.

In certain embodiments, pharmaceutical compositions are administered by intracerebroventricular (ICV) injection or infusion. Intracerebroventricular, or intraventricular, delivery of a pharmaceutical composition comprising one or more antisense compounds may be performed in any one or more of the brain's ventricles, which are filled with cerebrospinal fluid (CSF). CSF is a clear fluid that fills the ventricles, is present in the subarachnoid space, and surrounds the brain and spinal cord. CSF is produced by the choroid plexuses and via the weeping or transmission of tissue fluid by the brain into the ventricles. The choroid plexus is a structure lining the floor of the lateral ventricle and the roof of the third and fourth ventricles. Certain studies have indicated that these structures are capable of producing 400-600 ccs of fluid per day consistent with an amount to fill the central nervous system spaces four times in a day. In adult humans, the volume of this fluid has been calculated to be from 125 to 150 ml (4-5 oz). The CSF is in continuous formation, circulation and absorption. Certain studies have indicated that approximately 430 to 450 ml (nearly 2 cups) of CSF may be produced every day. Certain calculations estimate that production equals approximately 0.35 ml per minute in adults and 0.15 per minute in infant humans. The choroid plexuses of the lateral ventricles produce the majority of CSF. It flows through the foramina of Monro into the third ventricle where it is added to by production from the third ventricle and continues down through the aqueduct of Sylvius to the fourth ventricle. The fourth ventricle adds more CSF; the fluid then travels into the subarachnoid space through the foramina of Magendie and Luschka. It then circulates throughout the base of the brain, down around the spinal cord and upward over the cerebral hemispheres. The CSF empties into the blood via the arachnoid villi and intracranial vascular sinuses.

In certain embodiments, such pharmaceutical compositions are administered systemically. In certain embodiments, pharmaceutical compositions are administered subcutaneously. In certain embodiments, pharmaceutical compositions are administered intravenously. In certain embodiments, pharmaceutical compositions are administered by intramuscular injection.

In certain embodiments, pharmaceutical compositions are administered both directly to the CSF (e.g., IT and/or ICV injection and/or infusion) and systemically.

In certain embodiments, an antisense compound administered systemically enters neurons. In certain embodiments, systemically administered antisense compounds may penetrate the blood-brain barrier, particularly in young subjects where the blood-brain barrier is not fully formed (e.g., in subjects in eutero and/or in newborn subjects). In certain embodiments, some amount of systemically administered antisense compound may be taken up by nerve cells, even in subjects in which the blood-brain barrier is fully formed. For example, antisense compounds may enter a neuron at or near the neuromuscular junction (retrograde uptake). In certain embodiments, such retrograde uptake results in antisense activity inside the neuron, including, but not limited to, a motor neuron, and provides a therapeutic benefit by antisense activity inside the neuron.

In certain embodiments, systemic administration provides therapeutic benefit by antisense activity occurring in cells and/or tissues other than neurons. While evidence suggests that functional SMN inside neurons is required for normal neuron function, the consequence of reduced functional SMN in other cells and tissues is not well characterized. In certain embodiments, antisense activity in non-neuronal cells results in restoration of SMN function in those non-neuronal cells, which in turn results in therapeutic benefit.

In certain embodiments, improved SMN function in non-neuronal cells provides improved neuronal cell function, whether or not SMN function inside neurons is improved. For example, in certain embodiments, systemic administration of pharmaceutical compositions of the present invention results in antisense activity in muscle cells. Such antisense activity in muscle cells may provide a benefit to the motor-neurons associated with that muscle cell or to neurons generally. In such embodiments, the muscle cell having restored SMN function may provide a factor that improves neuronal viability and/or function. In certain embodiments, such antisense activity is independent of benefit from antisense activity occurring from antisense compounds inside neurons. In certain embodiments, systemic administration of pharmaceutical compositions of the present invention results in antisense activity in other non-neuronal cells, including cells not in immediate association with neurons. Such antisense activity in non-neuronal cells may improve function of neurons. For example, antisense activity in a non-neuronal cell (e.g., liver cell) may result in that cell producing a factor that improves function of neurons. Note: since the term "antisense activity" includes direct and indirect activities, a benefit to neuronal function is an "antisense activity" even if no antisense compound enters the neuron.

In certain embodiments, systemic administration of a pharmaceutical composition results in therapeutic benefit independent of direct or indirect antisense activities in neurons. Typically, in the setting of SMA, neuronal function is diminished, resulting in significant symptoms. Additional symptoms may result from diminished SMN activity in other cells. Certain such symptoms may be masked by the relative severity of symptoms from diminished neuronal function. In certain embodiments, systemic administration results in restored or improved SMN function in non-neuronal cells. In certain such embodiments, such restored or improved SMN function in non-neuronal cells has therapeutic benefit. For example, in certain instances, subjects having SMA have reduced growth. Such reduced growth may not result from diminished function in neuronal cells. Indeed, reduced growth may be related to impaired function of cells in another organ, such as the pituitary gland, and/or may be the result of SMN deficiencies throughout the cells of the body. In such embodiments, systemic administration may result in improved SMN activity in pituitary cells and/or other cells, resulting in improved growth. In certain instances, administration to the CSF restores sufficient neuronal function to allow a subject to live longer, however one or more symptoms previously unknown because subjects typically died before such symptoms appeared emerges, because the subject lives longer. Certain such emergent symptoms may be lethal. In certain embodiments, emergent symptoms are treated by systemic administration. Regardless of mechanism, in certain embodiments, a variety of symptoms of SMA, including, but not limited to symptoms previously masked by more severe symptoms associated with impaired neuronal function, may be treated by systemic administration.

In certain embodiments, systemic administration of pharmaceutical compositions of the present invention result in increased SMN activity in muscle cells. In certain embodiments, such improved SMN activity in muscle cells provides therapeutic benefit. Improved SMN activity in muscle alone has been reported to be insufficient to provide therapeutic benefit (e.g., Gravrilina, et al., Hum Mol Genet 2008 17(8): 1063-1075). In certain embodiments, the present invention provides methods that result improve SMN function in muscle and do provide therapeutic benefit. In certain instances, therapeutic benefit may be attributable to improved SMN function in other cells (alone or in combination with muscle cells). In certain embodiments, improved SMN function in muscle alone may provide benefit.

In certain embodiments, systemic administration results in improved survival.

6. Spinal Muscular Atrophy (SMA)

SMA is a genetic disorder characterized by degeneration of spinal motor neurons. SMA is caused by the homozygous loss of both functional copies of the SMN1 gene. However, the SMN2 gene has the potential to code for the same protein as SMN1 and thus overcome the genetic defect of SMA patients. SMN2 contains a translationally silent mutation (C→T) at position +6 of exon 7, which results in inefficient inclusion of exon 7 in SMN2 transcripts. Therefore, the predominant form of SMN2, one which lacks exon 7, is unstable and inactive. Thus, therapeutic compounds capable of modulating SMN2 splicing such that the percentage of SMN2 transcripts containing exon 7 is increased, would be useful for the treatment of SMA.

In certain embodiments, the present invention provides antisense compounds complementary to a pre-mRNA encoding SMN2. In certain such embodiments, the antisense compound alters splicing of SMN2. Certain sequences and regions useful for altering splicing of SMN2 may be found in PCT/US06/024469, which is hereby incorporated by reference in its entirety for any purpose. In certain embodiments, oligomeric compounds having any motif described herein have a nucleobase sequence complementary to intron 7 of SMN2. Certain such nucleobase sequences are exemplified in the non-limiting table below. In the nucleobase sequences exemplified in the non-limiting table below, all "C" residues represent 5-methylcytosines.

| Sequence | Length | SEQ ID NO |
|---|---|---|
| TGCTGGCAGACTTAC | 15 | 3 |
| CATAATGCTGGCAGA | 15 | 4 |
| TCATAATGCTGGCAG | 15 | 5 |
| TTCATAATGCTGGCA | 15 | 6 |
| TTTCATAATGCTGGC | 15 | 2 |
| ATTCACTTTCATAATGCTGG | 20 | 7 |
| TCACTTTCATAATGCTGG | 18 | 1 |
| CTTTCATAATGCTGG | 15 | 8 |
| TCATAATGCTGG | 12 | 9 |
| ACTTTCATAATGCTG | 15 | 10 |
| TTCATAATGCTG | 12 | 11 |
| CACTTTCATAATGCT | 15 | 12 |
| TTTCATAATGCT | 12 | 13 |
| TCACTTTCATAATGC | 15 | 14 |
| CTTTCATAATGC | 12 | 15 |
| TTCACTTTCATAATG | 15 | 16 |
| ACTTTCATAATG | 12 | 17 |
| ATTCACTTTCATAAT | 15 | 18 |
| CACTTTCATAAT | 12 | 19 |
| GATTCACTTTCATAA | 15 | 20 |
| TCACTTTCATAA | 12 | 21 |
| TTCACTTTCATA | 12 | 22 |

-continued

| Sequence | Length | SEQ ID NO |
|---|---|---|
| ATTCACTTTCAT | 12 | 23 |
| AGTAAGATTCACTTT | 15 | 24 |

Antisense compounds of the present invention can be used to modulate the expression of SMN2 in a subject, such as a human. In certain embodiments, the subject has spinal muscular atrophy. In certain such subjects, the SMN1 gene is absent or otherwise fails to produce sufficient amounts of functional SMN protein. In certain embodiments, the antisense compounds of the present invention effectively modulate splicing of SMN2, resulting in an increase in exon 7 inclusion in SMN2 mRNA and ultimately in SMN2 protein that includes the amino acids corresponding to exon 7. Such alternate SMN2 protein resembles wild-type SMN protein. Antisense compounds of the present invention that effectively modulate expression of SMN2 mRNA or protein products of expression are considered active antisense compounds.

Modulation of expression of SMN2 can be measured in a bodily fluid, which may or may not contain cells; tissue; or organ of the animal. Methods of obtaining samples for analysis, such as body fluids (e.g., sputum, serum, CSF), tissues (e.g., biopsy), or organs, and methods of preparation of the samples to allow for analysis are well known to those skilled in the art. Methods for analysis of RNA and protein levels are discussed above and are well known to those skilled in the art. The effects of treatment can be assessed by measuring biomarkers associated with the target gene expression in the aforementioned fluids, tissues or organs, collected from an animal contacted with one or more compounds of the invention, by routine clinical methods known in the art.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of SMN2 expression in the cells of bodily fluids, organs or tissues. An effective amount can be determined by monitoring the modulatory effect of the antisense compound or compounds or compositions on target nucleic acids or their products by methods routine to the skilled artisan.

The invention also provides an antisense compound as described herein, for use in any of the methods as described herein. For example, the invention provides an antisense compound comprising an antisense oligonucleotide complementary to a nucleic acid encoding human SMN2, for use in treating a disease or condition associated with survival motor neuron protein (SMN), such as spinal muscular atrophy (SMA). As a further example, the invention provides an antisense compound comprising an antisense oligonucleotide complementary to a nucleic acid encoding human SMN2, for use in treating a disease or condition associated with survival motor neuron protein (SMN) by administering the antisense compound directly into the central nervous system (CNS) or CSF.

The invention also provides the use of an antisense compound as described herein in the manufacture of a medicament for use in any of the methods as described herein. For example, the invention provides the use of an antisense compound comprising an antisense oligonucleotide complementary to a nucleic acid encoding human SMN2 in the manufacture of a medicament for treating a disease or condition associated with survival motor neuron protein (SMN), such as spinal muscular atrophy (SMA). As a further example, the invention provides the use of an antisense compound comprising an antisense oligonucleotide complementary to a nucleic acid encoding human SMN2 in the manufacture of a medicament for treating a disease or condition associated with survival motor neuron protein (SMN) by administration of the medicament directly into the central nervous system (CNS) or CSF.

In certain embodiments, oligomeric compounds having any motif described herein have a nucleobase sequence complementary to exon 7 of SMN2.

In certain embodiments, oligomeric compounds having any motif described herein have a nucleobase sequence complementary to intron 6 of SMN2.

In certain embodiments, an antisense compound comprises an antisense oligonucleotide having a nucleobase sequence comprising at least 10 nucleobases of the sequence: TCACTTTCATAATGCTGG (SEQ ID NO: 1). In certain embodiments, an antisense oligonucleotide has a nucleobase sequence comprising at least 11 nucleobases of such sequence. In certain embodiments, an antisense oligonucleotide has a nucleobase sequence comprising at least 12 nucleobases of such sequence. In certain embodiments, an antisense oligonucleotide has a nucleobase sequence comprising at least 13 nucleobases of such sequence. In certain embodiments, an antisense oligonucleotide has a nucleobase sequence comprising at least 14 nucleobases of such sequence. In certain embodiments, an antisense oligonucleotide has a nucleobase sequence comprising at least 15 nucleobases of such sequence. In certain embodiments, an antisense oligonucleotide has a nucleobase sequence comprising at least 16 nucleobases of such sequence. In certain embodiments, an antisense oligonucleotide has a nucleobase sequence comprising at least 17 nucleobases of such sequence. In certain embodiments, an antisense oligonucleotide has a nucleobase sequence comprising the nucleobases of such sequence. In certain embodiments, an antisense oligonucleotide has a nucleobase sequence consisting of the nucleobases of such sequence. In certain embodiments, an antisense oligonucleotide consists of 10-18 linked nucleosides and has a nucleobase sequence 100% identical to an equal-length portion of the sequence: TCACTTTCATAATGCTGG (SEQ ID NO: 1).

7. Certain Subjects

In certain embodiments, a subject has one or more indicator of SMA. In certain embodiments, the subject has reduced electrical activity of one or more muscles. In certain embodiments, the subject has a mutant SMN1 gene. In certain embodiment, the subject's SMN1 gene is absent or incapable of producing functional SMN protein. In certain embodiments, the subject is diagnosed by a genetic test. In certain embodiments, the subject is identified by muscle biopsy. In certain embodiments, a subject is unable to sit upright. In certain embodiments, a subject is unable to stand or walk. In certain embodiments, a subject requires assistance to breathe and/or eat. In certain embodiment, a subject is identified by electrophysiological measurement of muscle and/or muscle biopsy.

In certain embodiments, the subject has SMA type I. In certain embodiments, the subject has SMA type II. In certain embodiments, the subject has SMA type III. In certain embodiments, the subject is diagnosed as having SMA in utero. In certain embodiments, the subject is diagnosed as having SMA within one week after birth. In certain embodiments, the subject is diagnosed as having SMA within one month of birth. In certain embodiments, the subject is diagnosed as having SMA by 3 months of age. In certain embodiments, the subject is diagnosed as having SMA by 6 months of age. In certain embodiments, the subject is diagnosed as having SMA by 1 year of age. In certain embodiments, the subject is diagnosed as having SMA between 1 and 2 years of age. In certain embodiments, the subject is diagnosed as having SMA between 1 and 15 years of age. In certain embodiments, the subject is diagnosed as having SMA when the subject is older than 15 years of age.

In certain embodiments, the first dose of a pharmaceutical composition according to the present invention is administered in utero. In certain such embodiments, the first dose is administered before complete development of the blood-brain-barrier. In certain embodiments, the first dose is administered to the subject in utero systemically. In certain embodiments, the first dose is administered in utero after formation of the blood-brain-barrier. In certain embodiments, the first dose is administered to the CSF.

In certain embodiments, the first dose of a pharmaceutical composition according to the present invention is administered when the subject is less than one week old. In certain embodiments, the first dose of a pharmaceutical composition according to the present invention is administered when the subject is less than one month old. In certain embodiments, the first dose of a pharmaceutical composition according to the present invention is administered when the subject is less than 3 months old. In certain embodiments, the first dose of a pharmaceutical composition according to the present invention is administered when the subject is less than 6 months old. In certain embodiments, the first dose of a pharmaceutical composition according to the present invention is administered when the subject is less than one year old. In certain embodiments, the first dose of a pharmaceutical composition according to the present invention is administered when the subject is less than 2 years old. In certain embodiments, the first dose of a pharmaceutical composition according to the present invention is administered when the subject is less than 15 years old. In certain embodiments, the first dose of a pharmaceutical composition according to the present invention is administered when the subject is older than 15 years old.

8. Certain Doses

In certain embodiments, the present invention provides dose amounts and frequencies. In certain embodiments, pharmaceutical compositions are administered as a bolus injection.

In certain embodiments, pharmaceutical compositions are administered as a single IT bolus lumbar puncture injection. In certain embodiments, the IT bolus lumbar puncture injection target site for needle insertion is the L3/L4 space. In certain embodiments, the IT bolus lumbar puncture injection target site for needle insertion is the L3/L4 space but may be 1 segment above or 1-2 segments below this level, if needed. In certain embodiments, the volume of the IT bolus lumbar puncture injection is 5 mL. In certain embodiments, the volume of the IT bolus lumbar puncture injection is 1 mL. In certain embodiments, the volume of the IT bolus lumbar puncture injection is 2 mL. In certain embodiments, the volume of the IT bolus lumbar puncture injection is 3 mL. In certain embodiments, the volume of the IT bolus lumbar puncture injection is 4 mL. In certain embodiments, the volume of the IT bolus lumbar puncture injection is 6 mL. In certain embodiments, the volume of the IT bolus lumbar puncture injection is 7 mL. In certain embodiments, the volume of the IT bolus lumbar puncture injection is 8 mL. In certain embodiments, the volume of the IT bolus lumbar puncture injection is 9 mL. In certain embodiments, the volume of the IT bolus lumbar puncture injection is 10 mL. In certain embodiments, the volume of the IT bolus lumbar puncture injection is 4.3 mL. In certain embodiments, the volume of the IT bolus lumbar puncture injection is 4.5 mL.

9. Administration of Certain Doses

In certain embodiments, the dose is selected to produce a desired tissue concentration. In certain embodiments, the desired tissue is spinal cord tissue. In certain embodiments, the desired spinal cord tissue concentration is between 1µ/g and 10 µ/g. In certain embodiments, the desired spinal cord tissue concentration is between 1 µ/g and 15 µ/g. In certain embodiments, the desired spinal cord tissue concentration is between 1 µ/g and 14 µ/g. In certain embodiments, the desired spinal cord tissue concentration is between 1 µ/g and 13 µ/g. In certain embodiments, the desired spinal cord tissue concentration is between 1 µ/g and 12 µ/g. In certain embodiments, the desired spinal cord tissue concentration is between 1 µ/g and 11 µ/g. In certain embodiments, the desired spinal cord tissue concentration is between 1 µ/g and 9 µ/g. In certain embodiments, the desired spinal cord tissue concentration is between 1 µ/g and 8 µ/g. In certain embodiments, the desired spinal cord tissue concentration is between 1 µ/g and 7 µ/g. In certain embodiments, the desired spinal cord tissue concentration is between 1 µ/g and 6 µ/g. In certain embodiments, the desired spinal cord tissue concentration is between 1 µ/g and 5 µ/g. In certain embodiments, the desired spinal cord tissue concentration is between 1 µ/g and 4 µ/g. In certain embodiments, the desired spinal cord tissue concentration is between 1 µ/g and 3 µ/g. In certain embodiments, the desired spinal cord tissue concentration is between 1 µ/g and 2 µ/g.

10. Certain Routes of Administration

In certain embodiments, a dose is administered as an intrathecal injection by lumbar puncture. In certain embodiments, a single dose is administered as an intrathecal injection by lumbar puncture. In certain embodiments, a single dose of ISIS 396443 is administered as an intrathecal injection by lumbar puncture. In certain embodiments, a single 0.1 to 15 milligram dose of ISIS 396443 is administered as an intrathecal injection by lumbar puncture. In certain embodiments, a single 1 milligram dose of ISIS 396443 is administered as an intrathecal injection by lumbar puncture. In certain embodiments, a single 2 milligram dose of ISIS 396443 is administered as an intrathecal injection by lumbar puncture. In certain embodiments, a single 3 milligram dose of ISIS 396443 is administered as an intrathecal injection by lumbar puncture. In certain embodiments, a single 4 milligram dose of ISIS 396443 is administered as an intrathecal injection by lumbar puncture. In certain embodiments, a single 5 milligram dose of ISIS 396443 is administered as an intrathecal injection by lumbar puncture. In certain embodiments, a single 6 milligram dose of ISIS 396443 is administered as an intrathecal injection by lumbar puncture. In certain embodiments, a single 7 milligram dose of ISIS 396443 is administered as an intrathecal injection by lumbar puncture. In certain embodiments, a single 8 milligram dose of ISIS 396443 is administered as an intrathecal injection by lumbar puncture. In certain embodiments, a single 9 milligram dose of ISIS 396443 is administered as an intrathecal injection by lumbar puncture. In certain embodiments, a single 10 milligram dose of ISIS 396443 is administered as an intrathecal injection by lumbar puncture. In certain embodiments, a single 11 milligram dose of ISIS 396443 is administered as an intrathecal injection by lumbar puncture. In certain embodiments, a single 12 milligram dose of ISIS 396443 is administered as an intrathecal injection by lumbar puncture. In certain embodiments, a single 13 milligram dose of ISIS 396443 is administered as an intrathecal injection by lumbar puncture. In certain embodiments, a single 14 milligram dose of ISIS 396443 is administered as an intrathecal injection by lumbar puncture. In certain embodiments, a single 15 milligram dose of ISIS 396443 is administered as an intrathecal injection by lumbar puncture.

In certain embodiments, a single 4.8 milligram dose of ISIS 396443 is administered as an intrathecal injection by lumbar puncture. In certain embodiments, a single 5.16 milligram dose of ISIS 396443 is administered as an intrathecal injection by lumbar puncture. In certain embodiments, a single 5.40 milligram dose of ISIS 396443 is administered as an intrathecal injection by lumbar puncture. In certain embodiments, a single 7.2 milligram dose of ISIS 396443 is administered as an intrathecal injection by lumbar puncture. In certain embodiments, a single 7.74 milligram dose of ISIS 396443 is administered as an intrathecal injection by lumbar puncture. In certain embodiments, a single 8.10 milligram dose of ISIS 396443 is administered as an intrathecal injection by lumbar puncture.

In certain embodiments, a single 9.6 milligram dose of ISIS 396443 is administered as an intrathecal injection by lumbar puncture. In certain embodiments, a single 10.32 milligram dose of ISIS 396443 is administered as an intrathecal injection by lumbar puncture. In certain embodiments, a single 10.80 milligram dose of ISIS 396443 is administered as an intrathecal injection by lumbar puncture. In certain embodiments, a single 11.30 milligram dose of ISIS 396443 is administered as an intrathecal injection by lumbar puncture. In certain embodiments, a single 12 milligram dose of ISIS 396443 is administered as an intrathecal injection by lumbar puncture. In certain embodiments, a single 12.88 milligram dose of ISIS 396443 is administered as an intrathecal injection by lumbar puncture. In certain embodiments, a single 13.5 milligram dose of ISIS 396443 is administered as an intrathecal injection by lumbar puncture. In certain embodiments, a single 14.13 milligram dose of ISIS 396443 is administered as an intrathecal injection by lumbar puncture.

In certain embodiments, where a dose of ISIS 396443 is administered as an intrathecal injection by lumbar puncture the use of a smaller gauge needle may reduce or ameliorate one or more symptoms associated with a lumbar puncture procedure. In certain embodiments, symptoms associated with a lumbar puncture include, but are not limited to, post-lumbar puncture syndrome, headache, back pain, pyrexia, constipation, nausea, vomiting, and puncture site pain. In certain embodiments, use of a 24 or 25 gauge needle for the lumbar puncture reduces or ameliorates one or more post lumbar puncture symptoms. In certain embodiments, use of a 21, 22, 23, 24 or 25 gauge needle for the lumbar puncture reduces or ameliorates post-lumbar puncture syndrome, headache, back pain, pyrexia, constipation, nausea, vomiting, and/or puncture site pain.

11. Certain Dose Concentrations and Injection Volumes

In certain embodiments, an active drug product, e.g. ISIS 396443, is combined with one or more pharmaceutically acceptable excipients or diluents. In certain embodiments, an active drug product, e.g. ISIS 396443, is combined with an artificial CSF diluent. In certain embodiments, ISIS 396443 is combined with an artificial CSF diluent. In certain embodiments, the concentration of ISIS 396443 in an artificial CSF diluent is 0.5 mg of ISIS 396443 per mL of solution. In certain embodiments, the concentration of ISIS 396443 in an artificial CSF diluent is 0.6 mg of ISIS 396443 per mL of solution. In certain embodiments, the concentration of ISIS 396443 in an artificial CSF diluent is 0.7 mg of ISIS 396443 per mL of solution. In certain embodiments, the concentration of ISIS 396443 in an artificial CSF diluent is 0.8 mg of ISIS 396443 per mL of solution. In certain embodiments, the concentration of ISIS 396443 in an artificial CSF diluent is 0.9 mg of ISIS 396443 per mL of solution. In certain embodiments, the concentration of ISIS 396443 in an artificial CSF diluent is 1.0 mg of ISIS 396443 per mL of solution. In certain embodiments, the concentration of ISIS 396443 in an artificial CSF diluent is 1.1 mg of ISIS 396443 per mL of solution. In certain embodiments, the concentration of ISIS 396443 in an artificial CSF diluent is 1.2 mg of ISIS 396443 per mL of solution. In certain embodiments, the concentration of ISIS 396443 in an artificial CSF diluent is 1.3 mg of ISIS 396443 per mL of solution. In certain embodiments, the concentration of ISIS 396443 in an artificial CSF diluent is 1.4 mg of ISIS 396443 per mL of solution. In certain embodiments, the concentration of ISIS 396443 in an artificial CSF diluent is 1.5 mg of ISIS 396443 per mL of solution. In certain embodiments, the concentration of ISIS 396443 in an artificial CSF diluent is 2.4 mg of ISIS 396443 per mL of solution.

In certain embodiments, the concentration of ISIS 396443 in an artificial CSF diluent is 0.2 mg of ISIS 396443 per mL of solution and the injection volume is 5.0 mL. In certain embodiments, the concentration of ISIS 396443 in an artificial CSF diluent is 0.6 mg of ISIS 396443 per mL of solution and the injection volume is 5.0 mL. In certain embodiments, the concentration of ISIS 396443 in an artificial CSF diluent is 1.2 mg of ISIS 396443 per mL of solution and the injection volume is 5.0 mL. In certain embodiments, the concentration of ISIS 396443 in an artificial CSF diluent is 1.8 mg of ISIS 396443 per mL of solution and the injection volume is 5.0 mL. In certain embodiments, the concentration of ISIS 396443 in an artificial CSF diluent is 2.0 mg of ISIS 396443 per mL of solution and the injection volume is 5.0 mL. In certain embodiments, the concentration of ISIS 396443 in an artificial CSF diluent is 2.4 mg of ISIS 396443 per mL of solution and the injection volume is 4.0 mL. In certain embodiments, the concentration of ISIS 396443 in an artificial CSF diluent is 2.4 mg of ISIS 396443 per mL of solution and the injection volume is 4.3 mL. In certain embodiments, the concentration of ISIS 396443 in an artificial CSF diluent is 2.4 mg of ISIS 396443 per mL of solution and the injection volume is 4.5 mL. In certain embodiments, the concentration of ISIS 396443 in an artificial CSF diluent is 2.4 mg of ISIS 396443 per mL of solution and the injection volume is 4.7 mL.

In certain embodiments, the concentration of ISIS 396443 in an artificial CSF diluent is 3 mg of ISIS 396443 per mL of solution and the injection volume is 4.0 mL. In certain embodiments, the concentration of ISIS 396443 in an artificial CSF diluent is 3 mg of ISIS 396443 per mL of solution and the injection volume is 4.3 mL. In certain embodiments, the concentration of ISIS 396443 in an artificial CSF diluent is 3 mg of ISIS 396443 per mL of solution and the injection volume is 4.5 mL. In certain embodiments, the concentration of ISIS 396443 in an artificial CSF diluent is 3 mg of ISIS 396443 per mL of solution and the injection volume is 4.7 mL.

In certain embodiments, a dose equivalent of ISIS 396443 is calculated based on a patient's age or weight. For example, in certain embodiments a dose may be 6 mg and the dose equivalent may be greater than 6 mg or less than 6 mg.

In certain embodiments, the dose and/or the volume of the injection will be adjusted based on the patient's age. In certain embodiments, the dose and/or the volume of the injection will be adjusted based on the patient's CSF volume. In certain embodiments, the dose and/or the volume of the injection will be adjusted based on the patient's age and/or estimated CSF volume. In certain embodiments, the volume of the injection is adjusted such that each patient will receive a 6 mg or 9 mg equivalent dose based on CSF volume scaling. (For example, see Matsuzawa J, Matsui M, Konishi T, Noguchi K, Gur R C, Bilker W, Miyawaki T. Age-related volumetric changes of brain gray and white matter in healthy infants and children. Cereb Cortex 2001 April; 11(4):335-342, which is hereby incorporated by reference in its entirety). In certain embodiments, the volume of the injection is adjusted such that each patient will receive a 12 mg equivalent dose based on CSF volume scaling. (For example, see Matsuzawa J, Matsui M, Konishi T, Noguchi K, Gur R C, Bilker W, Miyawaki T. Age-related volumetric changes of brain gray and white matter in healthy infants and children. Cereb Cortex 2001 April; 11(4):335-342, which is hereby incorporated by reference in its entirety).

12. Certain Dose Frequencies

In certain embodiments, multiple doses of ISIS 396443 are administered to a subject having one or more symptoms associated with SMA. In certain embodiments, two or more doses of ISIS 396443 are administered to a subject having one or more symptoms associated with SMA. In certain embodiments, three or more doses of ISIS 396443 are administered to a subject having one or more symptoms associated with SMA. In certain embodiments, multiple doses of ISIS 396443 are administered to a subject having one or more symptoms associated with SMA. In certain embodiments, multiple doses of ISIS 396443 are administered at the same interval to a subject having one or more symptoms associated with SMA. In certain embodiments, multiple doses of ISIS 396443 are administered at different intervals to a subject having one or more symptoms associated with SMA.

In certain embodiments, doses of ISIS 396443 are administered at intervals to a subject having one or more symptoms associated with SMA. In certain embodiments, single doses of ISIS 396443 are administered at 15 day intervals to a subject having one or more symptoms associated with SMA. In certain embodiments, single doses of ISIS 396443 are administered at 29 day intervals to a subject having one or more symptoms associated with SMA. In certain embodiments, single doses of ISIS 396443 are administered at 85 day intervals to a subject having one or more symptoms associated with SMA.

In certain embodiments a first dose of ISIS 396443 is administered to a subject having one or more symptoms associated with SMA, and a second dose of ISIS 396443 is administered about 15 days after the first dose. In certain embodiments a first dose of ISIS 396443 is administered to a subject having one or more symptoms associated with SMA, a second dose of ISIS 396443 is administered about 15 days after the first dose, and a third dose of ISIS 396443 is administered about 29 days after the first dose.

In certain embodiments a first dose of ISIS 396443 is administered to a subject having one or more symptoms associated with SMA, a second dose of ISIS 396443 is administered about 15 days after the first dose, a third dose of ISIS 396443 is administered about 29 days after the first dose, and a fourth dose of ISIS 396443 is administered about 211 days after the first dose.

In certain embodiments, single 3 mg doses of ISIS 396443 are administered at 15 day intervals to a subject having one or more symptoms associated with SMA. In certain embodiments, single 3 mg doses of ISIS 396443 are administered at 29 day intervals to a subject having one or more symptoms associated with SMA. In certain embodiments, single 6 mg doses of ISIS 396443 are administered at 85 day intervals to a subject having one or more symptoms associated with SMA.

In certain embodiments, single 9 mg doses of ISIS 396443 are administered at 29 day intervals to a subject having one or more symptoms associated with SMA. In certain embodiments, single 9 mg doses of ISIS 396443 are administered at 85 day intervals to a subject having one or more symptoms associated with SMA.

In certain embodiments, a first dose of ISIS 396443 is administered to a subject having one or more symptoms associated with SMA and a second dose of ISIS 396443 is administered 15 days after the first dose. In certain embodiments, a first dose of ISIS 396443 is administered to a subject having one or more symptoms associated with SMA and a second dose of ISIS 396443 is administered 29 days after the first dose. In certain embodiments, a first dose of ISIS 396443 is administered to a subject having one or more symptoms associated with SMA and a second dose of ISIS 396443 is administered about 1 month after the first dose. In certain embodiments, a first dose of ISIS 396443 is administered to a subject having one or more symptoms associated with SMA and a second dose of ISIS 396443 is administered about 4 weeks after the first dose. In certain embodiments, a first dose of ISIS 396443 is administered to a subject having one or more symptoms associated with SMA and a second dose of ISIS 396443 is administered 29 days after the first dose, and a third dose of ISIS 396443 is administered 85 days after the first dose. In certain embodiments, a first dose of ISIS 396443 is administered to a subject having one or more symptoms associated with SMA and a second dose of ISIS 396443 is administered 85 days after the first dose. In certain embodiments, a first dose of ISIS 396443 is administered to a subject having one or more symptoms associated with SMA and a second dose of ISIS 396443 is administered 85 days after the first dose. In certain embodiments, the first dose and the second dose are the same amount. In certain embodiments, the first dose and the second dose are different amounts. In certain embodiments, the first, second, and third dose are the same amount. In certain embodiments, the first, second, and third dose are different amounts.

In certain embodiments, a first dose of 3 mg of ISIS 396443 is administered to a subject having one or more symptoms associated with SMA, a second dose of 3 mg of ISIS 396443 is administered 29 days after the first dose, and a third dose of 3 mg of ISIS 396443 is administered 85 days after the first dose. In certain embodiments, a first dose of 6 mg of ISIS 396443 is administered to a subject having one or more symptoms associated with SMA, a second dose of 6 mg of ISIS 396443 is administered 29 days after the first dose, and a third dose of 6 mg of ISIS 396443 is administered 85 days after the first dose. In certain embodiments, a first dose of 9 mg of ISIS 396443 is administered to a subject having one or more symptoms associated with SMA, a second dose of 9 mg of ISIS 396443 is administered 29 days after the first dose, and a third dose of 9 mg of ISIS 396443 is administered 85 days after the first dose. In certain embodiments, a first dose of 12 mg of ISIS 396443 is administered to a subject having one or more symptoms associated with SMA, a second dose of 12 mg of ISIS 396443 is administered 29 days after the first dose, and a third dose of 12 mg of ISIS 396443 is administered 85 days after the first dose. In certain embodiments, a first dose of 15 mg of ISIS 396443 is administered to a subject having one or more symptoms associated with SMA, a second dose of 15 mg of ISIS 396443 is administered 29 days after the first dose, and a third dose of 15 mg of ISIS 396443 is administered 85 days after the first dose.

In certain embodiments, a first dose of 3 mg of ISIS 396443 is administered to a subject having one or more symptoms associated with SMA, a second dose of 3 mg of ISIS 396443 is administered 15 days after the first dose, and a third dose of 3 mg of ISIS 396443 is administered 85 days after the first dose. In certain embodiments, a first dose of 6 mg of ISIS 396443 is administered to a subject having one or more symptoms associated with SMA, a second dose of 6 mg of ISIS 396443 is administered 15 days after the first dose, and a third dose of 6 mg of ISIS 396443 is administered 85 days after the first dose. In certain embodiments, a first dose of 9 mg of ISIS 396443 is administered to a subject having one or more symptoms associated with SMA, a second dose of 9 mg of ISIS 396443 is administered 15 days after the first dose, and a third dose of 9 mg of ISIS 396443 is administered 85 days after the first dose. In certain embodiments, a first dose of 12 mg of ISIS 396443 is administered to a subject having one or more symptoms associated with SMA, a second dose of 12 mg of ISIS 396443 is administered 15 days after the first dose, and a third dose of 12 mg of ISIS 396443 is administered 85 days after the first dose. In certain embodiments, a first dose of 15 mg of ISIS 396443 is administered to a subject having one or more symptoms associated with SMA, a second dose of 15 mg of ISIS 396443 is administered 15 days after the first dose, and a third dose of 15 mg of ISIS 396443 is administered 85 days after the first dose.

In certain embodiments, a first dose of 3 mg or equivalent of ISIS 396443 is administered to a subject having one or more symptoms associated with SMA, a second dose of 3 mg or equivalent of ISIS 396443 is administered 15 days after the first dose, and a third dose of 3 mg or equivalent of ISIS 396443 is administered 85 days after the first dose. In certain embodiments, a first dose of 6 mg or equivalent of ISIS 396443 is administered to a subject having one or more symptoms associated with SMA, a second dose of 6 mg or equivalent of ISIS 396443 is administered 15 days after the first dose, and a third dose of 6 mg or equivalent of ISIS 396443 is administered 85 days after the first dose. In certain embodiments, a first dose of 9 mg or equivalent of ISIS 396443 is administered to a subject having one or more symptoms associated with SMA, a second dose of 9 mg or equivalent of ISIS 396443 is administered 15 days after the first dose, and a third dose of 9 mg or equivalent of ISIS 396443 is administered 85 days after the first dose. In certain embodiments, a first dose of 12 mg or equivalent of ISIS 396443 is administered to a subject having one or more symptoms associated with SMA, a second dose of 12 mg or equivalent of ISIS 396443 is administered 15 days after the first dose, and a third dose of 12 mg or equivalent of ISIS 396443 is administered 85 days after the first dose. In certain embodiments, a first dose of 15 mg or equivalent of ISIS 396443 is administered to a subject having one or more symptoms associated with SMA, a second dose of 15 mg or equivalent of ISIS 396443 is administered 15 days after the first dose, and a third dose of 15 mg or equivalent of ISIS 396443 is administered 85 days after the first dose.

In certain embodiments, a first dose of 3 mg of ISIS 396443 is administered to a subject having one or more symptoms associated with SMA, and a second dose of 3 mg of ISIS 396443 is administered six months after the first dose, and a third dose of 3 mg of ISIS 396443 is administered 12 months after the first dose. In certain embodiments, a first dose of 6 mg of ISIS 396443 is administered to a subject having one or more symptoms associated with SMA, a second dose of 6 mg of ISIS 396443 is administered six months after the first dose, and a third dose of 6 mg of ISIS 396443 is administered 12 months after the first dose. In certain embodiments, a first dose of 9 mg of ISIS 396443 is administered to a subject having one or more symptoms associated with SMA, a second dose of 9 mg of ISIS 396443 is administered six months after the first dose, and a third dose of 9 mg of ISIS 396443 is administered 12 months after the first dose. In certain embodiments, a first dose of 12 mg of ISIS 396443 is administered to a subject having one or more symptoms associated with SMA, a second dose of 12 mg of ISIS 396443 is administered six months after the first dose, and a third dose of 12 mg of ISIS 396443 is administered 12 months after the first dose. In certain embodiments, a first dose of 15 mg of ISIS 396443 is administered to a subject having one or more symptoms associated with SMA, a second dose of 15 mg of ISIS 396443 is administered six months after the first dose, and a third dose of 15 mg of ISIS 396443 is administered 12 months after the first dose.

In certain embodiments, a first dose of 3 mg or equivalent of ISIS 396443 is administered to a subject having one or more symptoms associated with SMA, and a second dose of 3 mg or equivalent of ISIS 396443 is administered 12 months after the first dose. In certain embodiments, a first dose of 6 mg or equivalent of ISIS 396443 is administered to a subject having one or more symptoms associated with SMA, and a second dose of 6 mg or equivalent of ISIS 396443 is administered 12 months after the first dose. In certain embodiments, a first dose of 9 mg or equivalent of ISIS 396443 is administered to a subject having one or more symptoms associated with SMA, and a second dose of 9 mg or equivalent of ISIS 396443 is administered 12 months after the first dose. In certain embodiments, a first dose of 12 mg or equivalent of ISIS 396443 is administered to a subject having one or more symptoms associated with SMA, and a second dose of 12 mg or equivalent of ISIS 396443 is administered 12 months after the first dose. In certain embodiments, a first dose of 15 mg or equivalent of ISIS 396443 is administered to a subject having one or more symptoms associated with SMA, and a second dose of 15 mg or equivalent of ISIS 396443 is administered 12 months after the first dose.

In certain embodiments, a first dose of 3 mg or equivalent of ISIS 396443 is administered to a subject having one or more symptoms associated with SMA, and a second dose of 3 mg or equivalent of ISIS 396443 is administered 13 months after the first dose. In certain embodiments, a first dose of 6 mg or equivalent of ISIS 396443 is administered to a subject having one or more symptoms associated with SMA, and a second dose of 6 mg or equivalent of ISIS 396443 is administered 13 months after the first dose. In certain embodiments, a first dose of 9 mg or equivalent of ISIS 396443 is administered to a subject having one or more symptoms associated with SMA, and a second dose of 9 mg or equivalent of ISIS 396443 is administered 13 months after the first dose. In certain embodiments, a first dose of 12 mg or equivalent of ISIS 396443 is administered to a subject having one or more symptoms associated with SMA, and a second dose of 12 mg or equivalent of ISIS 396443 is administered 13 months after the first dose. In certain embodiments, a first dose of 15 mg or equivalent of ISIS 396443 is administered to a subject having one or more symptoms associated with SMA, and a second dose of 15 mg or equivalent of ISIS 396443 is administered 13 months after the first dose.

In certain embodiments, a first dose of 3 mg or equivalent of ISIS 396443 is administered to a subject having one or more symptoms associated with SMA, and a second dose of 3 mg or equivalent of ISIS 396443 is administered 14 months after the first dose. In certain embodiments, a first dose of 6 mg or equivalent of ISIS 396443 is administered to a subject having one or more symptoms associated with SMA, and a second dose of 6 mg or equivalent of ISIS 396443 is administered 14 months after the first dose. In certain embodiments, a first dose of 9 mg or equivalent of ISIS 396443 is administered to a subject having one or more symptoms associated with SMA, and a second dose of 9 mg or equivalent of ISIS 396443 is administered 14 months after the first dose. In certain embodiments, a first dose of 12 mg or equivalent of ISIS 396443 is administered to a subject having one or more symptoms associated with SMA, and a second dose of 12 mg or equivalent of ISIS 396443 is administered 14 months after the first dose. In certain embodiments, a first dose of 15 mg or equivalent of ISIS 396443 is administered to a subject having one or more symptoms associated with SMA, and a second dose of 15 mg or equivalent of ISIS 396443 is administered 14 months after the first dose.

In certain embodiments, a first dose of 3 mg or equivalent of ISIS 396443 is administered to a subject having one or more symptoms associated with SMA, and a second dose of 3 mg or equivalent of ISIS 396443 is administered 15 months after the first dose. In certain embodiments, a first dose of 6 mg or equivalent of ISIS 396443 is administered to a subject having one or more symptoms associated with SMA, and a second dose of 6 mg or equivalent of ISIS 396443 is administered 15 months after the first dose. In certain embodiments, a first dose of 9 mg or equivalent of ISIS 396443 is administered to a subject having one or more symptoms associated with SMA, and a second dose of 9 mg or equivalent of ISIS 396443 is administered 15 months after the first dose. In certain embodiments, a first dose of 12 mg or equivalent of ISIS 396443 is administered to a subject having one or more symptoms associated with SMA, and a second dose of 12 mg or equivalent of ISIS 396443 is administered 15 months after the first dose. In certain embodiments, a first dose of 15 mg or equivalent of ISIS 396443 is administered to a subject having one or more symptoms associated with SMA, and a second dose of 15 mg or equivalent of ISIS 396443 is administered 15 months after the first dose.

In certain embodiments, a first dose of 3 mg or equivalent of ISIS 396443 is administered to a subject having one or more symptoms associated with SMA, and subsequent doses of 3 mg or equivalent of ISIS 396443 are administered at 6 month intervals thereafter. In certain embodiments, a first dose of 6 mg or equivalent of ISIS 396443 is administered to a subject having one or more symptoms associated with SMA, and subsequent doses of 6 mg or equivalent of ISIS 396443 are administered at 6 month intervals thereafter. In certain embodiments, a first dose of 9 mg or equivalent of ISIS 396443 is administered to a subject having one or more symptoms associated with SMA, and subsequent doses of 9 mg or equivalent of ISIS 396443 are administered at 6 month intervals thereafter. In certain embodiments, a first dose of 12 mg or equivalent of ISIS 396443 is administered to a subject having one or more symptoms associated with SMA, and subsequent doses of 12 mg or equivalent of ISIS 396443 are administered at 6 month intervals thereafter. In certain embodiments, a first dose of 15 mg or equivalent of ISIS 396443 is administered to a subject having one or more symptoms associated with SMA, and subsequent doses of 15 mg or equivalent of ISIS 396443 are administered at 6 month intervals thereafter.

In certain embodiments, a first dose of 3 mg or equivalent of ISIS 396443 is administered to a subject having one or more symptoms associated with SMA, and subsequent doses of 3 mg or equivalent of ISIS 396443 are administered at 12 month intervals thereafter. In certain embodiments, a first dose of 6 mg or equivalent of ISIS 396443 is administered to a subject having one or more symptoms associated with SMA, and subsequent doses of 6 mg or equivalent of ISIS 396443 are administered at 12 month intervals thereafter. In certain embodiments, a first dose of 9 mg or equivalent of ISIS 396443 is administered to a subject having one or more symptoms associated with SMA, and subsequent doses of 9 mg or equivalent of ISIS 396443 are administered at 12 month intervals thereafter. In certain embodiments, a first dose of 12 mg or equivalent of ISIS 396443 is administered to a subject having one or more symptoms associated with SMA, and subsequent doses of 12 mg or equivalent of ISIS 396443 are administered at 12 month intervals thereafter. In certain embodiments, a first dose of 15 mg or equivalent of ISIS 396443 is administered to a subject having one or more symptoms associated with SMA, and subsequent doses of 15 mg or equivalent of ISIS 396443 are administered at 12 month intervals thereafter.

In certain embodiments, a first dose of 3 mg or equivalent of ISIS 396443 is administered to a subject having one or more symptoms associated with SMA, and subsequent doses of 3 mg or equivalent of ISIS 396443 are administered at 13 month intervals thereafter. In certain embodiments, a first dose of 6 mg or equivalent of ISIS 396443 is administered to a subject having one or more symptoms associated with SMA, and subsequent doses of 6 mg or equivalent of ISIS 396443 are administered at 13 month intervals thereafter. In certain embodiments, a first dose of 9 mg or equivalent of ISIS 396443 is administered to a subject having one or more symptoms associated with SMA, and subsequent doses of 9 mg or equivalent of ISIS 396443 are administered at 13 month intervals thereafter. In certain embodiments, a first dose of 12 mg or equivalent of ISIS 396443 is administered to a subject having one or more symptoms associated with SMA, and subsequent doses of 12 mg or equivalent of ISIS 396443 are administered at 13 month intervals thereafter. In certain embodiments, a first dose of 15 mg or equivalent of ISIS 396443 is administered to a subject having one or more symptoms associated with SMA, and subsequent doses of 15 mg or equivalent of ISIS 396443 are administered at 13 month intervals thereafter.

In certain embodiments, a first dose of 3 mg or equivalent of ISIS 396443 is administered to a subject having one or more symptoms associated with SMA, and subsequent doses of 3 mg or equivalent of ISIS 396443 are administered at 14 month intervals thereafter. In certain embodiments, a first dose of 6 mg or equivalent of ISIS 396443 is administered to a subject having one or more symptoms associated with SMA, and subsequent doses of 6 mg or equivalent of ISIS 396443 are administered at 14 month intervals thereafter. In certain embodiments, a first dose of 9 mg or equivalent of ISIS 396443 is administered to a subject having one or more symptoms associated with SMA, and subsequent doses of 9 mg or equivalent of ISIS 396443 are administered at 14 month intervals thereafter. In certain embodiments, a first dose of 12 mg or equivalent of ISIS 396443 is administered to a subject having one or more symptoms associated with SMA, and subsequent doses of 12 mg or equivalent of ISIS 396443 are administered at 14 month intervals thereafter. In certain embodiments, a first dose of 15 mg or equivalent of ISIS 396443 is administered to a subject having one or more symptoms associated with SMA, and subsequent doses of 15 mg or equivalent of ISIS 396443 are administered at 14 month intervals thereafter.

In certain embodiments, a first dose of 3 mg or equivalent of ISIS 396443 is administered to a subject having one or more symptoms associated with SMA, and subsequent doses of 3 mg or equivalent of ISIS 396443 are administered at 15 month intervals thereafter. In certain embodiments, a first dose of 6 mg or equivalent of ISIS 396443 is administered to a subject having one or more symptoms associated with SMA, and subsequent doses of 6 mg or equivalent of ISIS 396443 are administered at 15 month intervals thereafter. In certain embodiments, a first dose of 9 mg or equivalent of ISIS 396443 is administered to a subject having one or more symptoms associated with SMA, and subsequent doses of 9 mg or equivalent of ISIS 396443 are administered at 15 month intervals thereafter. In certain embodiments, a first dose of 12 mg or equivalent of ISIS 396443 is administered to a subject having one or more symptoms associated with SMA, and subsequent doses of 12 mg or equivalent of ISIS 396443 are administered at 15 month intervals thereafter. In certain embodiments, a first dose of 15 mg or equivalent of ISIS 396443 is administered to a subject having one or more symptoms associated with SMA, and subsequent doses of 15 mg or equivalent of ISIS 396443 are administered at 15 month intervals thereafter.

In certain embodiments, a first dose of 3 mg of ISIS 396443 is administered to a subject having one or more symptoms associated with SMA, a second dose of 3 mg of ISIS 396443 is administered 15 days after the first dose, a third dose of 3 mg of ISIS 396443 is administered 29 days after the first dose, and a fourth dose of 3 mg of ISIS 396443 is administered 211 days after the first dose. In certain embodiments, a first dose of 6 mg of ISIS 396443 is administered to a subject having one or more symptoms associated with SMA, a second dose of 6 mg of ISIS 396443 is administered 15 days after the first dose, a third dose of 6 mg of ISIS 396443 is administered 29 days after the first dose, and a fourth dose of 6 mg of ISIS 396443 is administered 211 days after the first dose. In certain embodiments, a first dose of 9 mg of ISIS 396443 is administered to a subject having one or more symptoms associated with SMA, a second dose of 9 mg of ISIS 396443 is administered 15 days after the first dose, a third dose of 9 mg of ISIS 396443 is administered 29 days after the first dose, and a fourth dose of 9 mg of ISIS 396443 is administered 211 days after the first dose. In certain embodiments, a first dose of 12 mg of ISIS 396443 is administered to a subject having one or more symptoms associated with SMA, a second dose of 12 mg of ISIS 396443 is administered 15 days after the first dose, a third dose of 12 mg of ISIS 396443 is administered 29 days after the first dose, and a fourth dose of 12 mg of ISIS 396443 is administered 211 days after the first dose. In certain embodiments, a first dose of 15 mg of ISIS 396443 is administered to a subject having one or more symptoms associated with SMA, a second dose of 15 mg of ISIS 396443 is administered 15 days after the first dose, a third dose of 15 mg of ISIS 396443 is administered 29 days after the first dose, and a fourth dose of 15 mg of ISIS 396443 is administered 211 days after the first dose.

Proposed dose frequency is approximate, for example, in certain embodiments if the proposed dose frequency is a dose at day 1 and a second dose at day 29, an SMA patient may receive a second dose 25, 26, 27, 28, 29, 30, 31, 32, 33, or 34 days after receipt of the first dose. In certain embodiments, if the proposed dose frequency is a dose at day 1 and a second dose at day 15, an SMA patient may receive a second dose 10, 11, 12, 13, 14, 15, 16, 17, 18, 19, or 20 days after receipt of the first dose. In certain embodiments, if the proposed dose frequency is a dose at day 1 and a second dose at day 85, an SMA patient may receive a second dose 80, 81, 82, 83, 84, 85, 86, 87, 88, 89, or 90 days after receipt of the first dose.

13. Co-Administration

In certain embodiments, pharmaceutical compositions of the present invention are co-administered with at least one other pharmaceutical composition for treating SMA and/or for treating one or more symptom associated with SMA. In certain embodiments, such other pharmaceutical composition is selected from trichostatin-A, valproic acid, riluzole, hydroxyurea, and a butyrate or butyrate derivative. In certain embodiments, pharmaceutical compositions of the present invention are co-administered with trichostatin A. In certain embodiments, pharmaceutical compositions of the present invention are co-administered with a derivative of quinazoline, for example as described in Thurmond, et al., J. Med Chem. 2008, 51, 449-469. In certain embodiments, a pharmaceutical composition of the present invention and at least one other pharmaceutical composition are co-administered at the same time. In certain embodiments, a pharmaceutical composition of the present invention and at least one other pharmaceutical composition are co-administered at different times.

In certain embodiments, pharmaceutical compositions of the present invention are co-administered with a gene therapy agent. In certain such embodiments, the gene therapy agent is administered to the CSF and the pharmaceutical composition of the present invention is administered systemically. In certain such embodiments, the gene therapy agent is administered to the CSF and the pharmaceutical composition of the present invention is administered to the CSF and systemically. In certain embodiments, a pharmaceutical composition of the present invention and a gene therapy agent are co-administered at the same time. In certain embodiments, a pharmaceutical composition of the present invention and a gene therapy agent are co-administered at different times. Certain gene therapy approaches to SMA treatment have been reported (e.g., Coady et al., PLoS ONE 2008 3(10): e3468; Passini et al., J Clin Invest 2010 April 1, 120(4): 1253-64).

In certain embodiments, pharmaceutical compositions of the present invention are co-administered with at least one other therapy for SMA. In certain embodiments, such other therapy for SMA is surgery. In certain embodiments, such other therapy is physical therapy, including, but not limited to exercises designed to strengthen muscles necessary for breathing, such as cough therapy. In certain embodiments, other therapy is a physical intervention, such as a feeding tube or device for assisted breathing.

In certain embodiments, pharmaceutical compositions of the present invention are co-administered with one or more other pharmaceutical compositions that reduce an undesired side-effect of the pharmaceutical compositions of the present invention.

14. Phenotypic Effects

In certain embodiments, administration of at least one pharmaceutical composition of the present invention results in a phenotypic change in the subject. In certain embodiments, such phenotypic changes include, but are not limited to: increased absolute amount of SMN mRNA that includes exon 7; increase in the ratio SMN mRNA that includes exon 7 to SMN mRNA lacking exon 7; increased absolute amount of SMN protein that includes exon 7; increase in the ratio SMN protein that includes exon 7 to SMN protein lacking exon 7; improved muscle strength, improved electrical activity in at least one muscle; improved respiration; weight gain; and survival. In certain embodiments, at least one phenotypic change is detected in a motoneuron of the subject. In certain embodiments, administration of at least one pharmaceutical composition of the present invention results in a subject being able to sit-up, to stand, and/or to walk. In certain embodiments, administration of at least one pharmaceutical composition of the present invention results in a subject being able to eat, drink, and/or breathe without assistance. In certain embodiments, efficacy of treatment is assessed by electrophysiological assessment of muscle. In certain embodiments, administration of a pharmaceutical composition of the present invention improves at least one symptom of SMA and has little or no inflammatory effect. In certain such embodiment, absence of inflammatory effect is determined by the absence of significant increase in Aifl levels upon treatment.

In certain embodiments, administration of at least one pharmaceutical composition of the present invention delays the onset of at least one symptom of SMA. In certain embodiments, administration of at least one pharmaceutical composition of the present invention slows the progression of at least one symptom of SMA. In certain embodiments, administration of at least one pharmaceutical composition of the present invention reduces the severity of at least one symptom of SMA.

In certain embodiments, administration of at least one pharmaceutical composition of the present disclosure to a subject having SMA results in the subject improving his or her Hammersmith Functional Motor Scale-Expanded (HFMSE). The HFMSE is a reliable and validated tool used to assess motor function in children with SMA. In certain embodiments, the HFMSE is used to assess responses on 33 motor function tasks, where each task is scored on a scale from 0 to 2. In certain embodiments, administration of at least one pharmaceutical composition of the present disclosure to a subject having SMA results in the subject improving his or her Pediatric Quality of Life Inventory (PedsQL™) Measurement 4.0 Generic Core Scales. In certain embodiments, administration of at least one pharmaceutical composition of the present disclosure to a subject having SMA results in the subject improving his or her Pediatric Quality of Life Inventory 3.0 Neuromuscular Modules. In certain embodiments, administration of at least one pharmaceutical composition of the present disclosure to a subject having SMA results in the subject improving his or her health-related quality of life. In certain embodiments, administration of at least one pharmaceutical composition of the present disclosure to a subject having SMA results in the subject improving his or her Compound Muscle Action Potential (CMAP). In certain embodiments, administration of at least one pharmaceutical composition of the present disclosure to a subject having SMA results in the subject improving his or her Motor Unit Number Estimation (MUNE). CMAP and MUNE are electrophysiological techniques that can be used to determine the approximate number of motor neurons in a muscle or group of muscles. MUNE methods also provide a means of measuring motor unit size, enabling tracking of the number of motor units and the compensatory phenomenon of collateral reinnervation. CMAP and MUNE are well validated methods for tracking disease progression in neuromuscular disorders such as spinal muscular atrophy and amyotrophic lateral sclerosis.

In certain embodiments, administration of at least one pharmaceutical composition of the present invention results in an undesired side-effect. In certain embodiments, a treatment regimen is identified that results in desired amelioration of symptoms while avoiding undesired side-effects.

15. Dosage Units

In certain embodiments pharmaceutical compositions of the present invention are prepared as dosage units for administration. Certain such dosage units are at concentrations selected from 0.01 mg to 100 mg. In certain such embodiments, a pharmaceutical composition of the present invention comprises a dose of antisense compound selected from 0.01 mg, 0.1 mg, 0.5 mg, 1 mg, 5 mg, 10 mg, 20 mg, 25 mg, 50 mg, 75 mg, 100 mg, 150 mg, and 200 mg. In certain embodiments, a pharmaceutical composition is comprises a dose of oligonucleotide selected from 0.1 mg, 0.5 mg, 1 mg, 5 mg, 10 mg, 25 mg, and 50 mg.

16. Kits

In certain embodiments, the present invention provides kits comprising at least one pharmaceutical composition. In certain embodiments, such kits further comprise a means of delivery, for example a syringe or infusion pump.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited herein is hereby incorporated by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified bases, such as "AT$^{me}$CGAUCG," wherein $^{me}$C indicates a cytosine base comprising a methyl group at the 5-position.

Example 1—Antisense Compounds Targeting SMN2

The following oligonucleotides were synthesized using standard techniques previously reported.

```
Reference # Sequence           Length  Chemistry     SEQ ID NO

ISIS396443  TCACTTTCATAATGCTGG  18      Full 2'-MOE;  1
                                        full PS ISIS396449  TTTCATAATGCTGGC     15      Full 2'-MOE;  2
                                        full PS
```

PS = phosphorothioate internucleoside linkages
All C residues are 5-methylcytosines.

Example 2—Single Administration Study of ISIS 396443

In a Phase 1 study involving 28 patients having SMA, patient therapy was commenced with a single administration of ISIS 396443. A single dose of ISIS 396443 was administered intrathecally as a lumbar puncture bolus injection using a spinal anesthesia needle between 21 gauge and 25 gauge. The dose amounts and number of patients receiving each dose are listed in the table below.

| Patient Group | # Patients | Dose (mg) |
|---|---|---|
| 1 | 6 | 1 |
| 2 | 6 | 3 |
| 3 | 6 | 6 |
| 4 | 10 | 9 |

ISIS 396443 was well tolerated at all dose levels tested. Additionally, at both 29 days and 85 days after receiving the single dose administration, patients were evaluated using the Hammersmith Motor Function Scale-Expanded (HFMSE). Patients that received the highest dose level of ISIS 396443 (9 mg) showed improvement in HFMSE scores. At day 85, the mean change from the baseline was +3.1 points on the HFMSE. 6 of the 10 patients receiving the highest dose demonstrated an improvement of greater than or equal to 4 points on the HFMSE (FIG. 1). Additionally, patients receiving the highest dose also demonstrated an increase in MUNE with stable CMAP at 85 days post-administration (see table below for the average change in the CMAP and MUNE neuromuscular electrophysiology measurements at 85 days post dose in patients receiving the highest dose of ISIS 396443).

| Neuromuscular Electrophysiology Measurement | Average Change in Neuromuscular Electrophysiology Measurement (N = 8) |
|---|---|
| CMAP | −0.38 |
| MUNE | 14.09 |

Follow-Up Analysis

Nine to 14 months after receiving the single dose administration, patients were evaluated using the Hammersmith Motor Function Scale-Expanded (HFMSE). SMA children receiving the highest doses of the drug (6 mg and 9 mg) continued to show improvements in muscle function tests up to 14 months after a single injection of the drug. The improvements in HFSME scores were dose dependent with the largest improvements observed in children in the highest dose cohort (9 mg, mean=5.75). Most children in the 9 mg dose cohort showed continuing improvements during follow up, with no children declining.

Additionally, no safety concerns related to of ISIS 396443 were identified in the long-term follow up (9-14 months after receiving the single dose administration of ISIS 396443) for patients from patient groups 1, 2, 3, and 4. The CSF analysis indicated no clinically meaningful changes at 9-14 months post-dose, and preliminary CSF pharmacokinetic analysis indicated detectable drug in the CSF at 9-14 months post-dose, consistent with the very long half-life of ISIS 396443 in the CNS.

Follow-Up Analysis MUNE & CMAP

Electrophysiology measurements of patients in Patient Group 4 (9 mg) demonstrated an increase in MUNE with a stable CMAP 9-14 months after receiving the single dose administration of ISIS 396443.

Follow-Up Analysis HFMSE Scores

Nine to 14 months after receiving the single dose administration, patients were evaluated using the Hammersmith Motor Function Scale-Expanded (HFMSE). The average HFMSE scores for patients receiving a 9 mg dose of ISIS 396443 on each of day 29, day 85, and at 9-14 months are presented in the table below. As the table below illustrates, the average HFMSE continued to improve post-dose.

| Patient Group | Time | Mean HFMSE (±SD) |
|---|---|---|
| 4 (9 mg dose) | Day 29 | 2.43 (±1.72) |
| 4 (9 mg dose) | Day 85 | 3.10 (±2.60) |
| 4 (9 mg dose) | 9-14 months | 5.75 (±4.40) |

Example 3—Multiple Administration Study of ISIS 396443

In a Phase 1/2a study involving 24 patients having SMA, patient therapy was commenced. ISIS 396443 was administered intrathecally as a lumbar puncture bolus injection using a spinal anesthesia needle between 21 gauge and 25 gauge. The dose amounts, number of patients receiving each dose, and proposed dose frequency for multiple doses are listed in the table below. Patients having SMA and receiving a dose of 3 mg or 6 mg have a dose frequency of receiving a second dose approximately 29 days after receiving a first dose and receiving a third dose approximately 85 days after receiving a first dose. Patients having SMA and receiving a dose of 9 mg have a dose frequency of receiving a second dose of ISIS 396443 approximately 85 days after receiving a first dose. In the table below "ND" stands for no dose. For example, SMA patients that receive a dose of 9 mg of ISIS 396443 on day 1 receive a second 9 mg dose of ISIS 396443 on day 85 and no dose of ISIS 396443 on day 29. Proposed dose frequency is approximate, for example, if the proposed dose frequency is a dose at day 1 and a second dose at day 29, an SMA patient may receive a second dose 25, 26, 27, 28, 29, 30, 31, 32, 33, or 34 days after receipt of the first dose.

In certain embodiments, SMA patients receiving one or more doses of ISIS 396443 are expected to remain stable or improve in one or more measures of SMA symptoms.

| Patient Group | # Patients | Dose at Day 1 (mg) | Dose at Day 29 (mg) | Dose at Day 85 (mg) |
|---|---|---|---|---|
| 1 | 8 | 3 | 3 | 3 |
| 2 | 8 | 6 | 6 | 6 |
| 3 | 8 | 9 | ND | 9 |

Example 4—Study of ISIS 396443 in Patients with Infant Onset SMA

A Phase 2 study involving 8 infant patients between 0 and 12 months of age and having infant onset SMA (also known as SMA Type I) was commenced. ISIS 396443 is to be administered intrathecally as a lumbar puncture bolus injection using a spinal anesthesia needle between 21 gauge and 25 gauge. The equivalent dose amounts, number of patients scheduled to receive each dose, adjusted dose, and proposed dose frequency for multiple doses are listed in the table below. The volume of the injection will be adjusted based on the patient's age per the table below. The volume of the injection is adjusted per the table below such that each patient will receive a 6 mg (Patient Group 1) or 12 mg (Patient Group 2) equivalent dose based on CSF volume scaling. (See Matsuzawa J, Matsui M, Konishi T, Noguchi K, Gur R C, Bilker W, Miyawaki T. Age-related volumetric changes of brain gray and white matter in healthy infants and children. Cereb Cortex 2001 April; 11(4):335-342). Patients having SMA type 1 and receiving an equivalent dose of 6 mg have a dose frequency of receiving a second 6 mg equivalent dose approximately 15 days after receiving a first dose and receiving a third 6 mg equivalent dose approximately 85 days after receiving a first dose. Patients having SMA type 1 and receiving an equivalent dose of 12 mg have a dose frequency of receiving a second 12 mg equivalent dose approximately 15 days after receiving a first dose and receiving a third 12 mg equivalent dose approximately 85 days after receiving a first dose. Proposed dose frequency is approximate, for example, if the proposed dose frequency is a dose at day 1 and a second dose at day 15, an SMA patient may receive a second dose 10, 11, 12, 13, 14, 15, 16, 17, 18, 19, or 20 days after receipt of the first dose.

In certain embodiments, SMA patients receiving one or more doses of ISIS 396443 are expected to remain stable or improve in one or more measures of SMA symptoms.

| Patient Group | # Patients | Equivalent Dose (mg) | Dose Frequency (Days) | Concentration (mg/mL) | Injection Volume |
|---|---|---|---|---|---|
| 1 | 4 | 6 | 1, 15, 85 | 1.2 | See Table below |
| 2 | 4 | 12 | 1, 15, 85 | 2.4 | See Table below |

| Age | Estimated CSF Volume | Injection Volume | Patient Group 1 Adjusted Dose | Patient Group 2 Adjusted Dose |
|---|---|---|---|---|
| 0-3 months | 120 mL | 4 mL | 4.8 mg | 9.60 mg |
| 3-6 months | 130 mL | 4.3 mL | 5.16 mg | 10.32 mg |
| 6-12 months | 135 mL | 4.5 mL | 5.40 mg | 10.80 mg |

Example 5—Study of ISIS 396443 in Patients with Infant Onset SMA

Using the protocol from example 4, an infant having infant onset SMA was successfully administered a 12 mg equivalent dose via a lumbar puncture bolus injection. The 12 mg equivalent dose by lumbar puncture bolus injection was administered without complication.

Example 6—Design of a Study of ISIS 396443 in Patients with Infant Onset SMA

ISIS 396443 is to be administered intrathecally as a lumbar puncture bolus injection using a spinal anesthesia needle between 21 gauge and 25 gauge. The equivalent dose amounts, number of patients scheduled to receive each dose, and proposed dose frequency for multiple doses are listed in the tables below. The volume of the injection will be adjusted based on the patient's age per the table below. The volume of the injection is adjusted per the table below such that each patient will receive a 12 mg (Patient Group 1) equivalent dose based on CSF volume scaling. (See Matsuzawa J, Matsui M, Konishi T, Noguchi K, Gur R C, Bilker W, Miyawaki T. Age-related volumetric changes of brain gray and white matter in healthy infants and children. Cereb Cortex 2001 April; 11(4):335-342).

Proposed dose frequency is approximate, for example, if the proposed dose frequency is a dose at day 1 and a second dose at day 15, an SMA patient may receive a second dose 10, 11, 12, 13, 14, 15, 16, 17, 18, 19, or 20 days after receipt of the first dose.

In certain embodiments, SMA patients receiving one or more doses of ISIS 396443 are expected to remain stable or improve in one or more measures of SMA symptoms.

| Patient Group | Equivalent Dose (mg) | Dose Frequency (Days) | Concentration (mg/mL) | Injection Volume |
|---|---|---|---|---|
| 1 | 12 | 1, 15, 29, 211 | 2.4 | See Table below |

| Age | Estimated CSF Volume | Injection Volume | Patient Group 1 Adjusted Dose |
|---|---|---|---|
| 0-3 months | 120 mL | 4 mL | 9.6 mg |
| 3-6 months | 130 mL | 4.3 mL | 10.32 mg |
| 6-12 months | 135 mL | 4.5 mL | 10.80 mg |
| 12-24 months | 140 mL | 4.7 mL | 11.3 |

What is claimed is:

1. A method of treating a human subject having spinal muscular atrophy (SMA), the method comprising administering to the human subject an antisense oligonucleotide consisting of 18 linked nucleosides, wherein the oligonucleotide has a nucleobase sequence consisting of the nucleobase sequence SEQ ID NO:1, wherein each internucleoside linkage of the oligonucleotide is a phosphorothioate linkage, wherein each nucleoside of the oligonucleotide is a 2'-MOE nucleoside, and wherein each cytosine of the oligonucleotide is a 5-methyl cytosine, wherein the antisense oligonucleotide is administered into the cerebrospinal fluid by bolus injection into the intrathecal space at a dose of 9.6, 10.3, 10.8, 11.3, or 12.0 milligrams of the antisense oligonucleotide.

2. The method of claim 1, wherein the administration is through a 21, 22, 23, 24, or 25 gauge needle.

3. The method of claim 1, wherein the administration is through a 22 gauge needle.

4. The method of claim 1, wherein the administration is between the L3 and L4 vertebrae.

5. The method of claim 1, wherein a 9.6 mg dose of the antisense oligonucleotide is administered in a volume of 4 mL, and wherein the dose is administered to the subject within 3 months of birth of the subject.

6. The method of claim 1, wherein a 10.3 mg dose of the antisense oligonucleotide is administered in a volume of 4.3 mL, and wherein the dose is administered to the subject between 3 and 6 months of birth of the subject.

7. The method of claim 1, wherein a 10.8 mg dose of the antisense oligonucleotide is administered in a volume of 4.5 mL, and wherein the dose is administered to the subject between 6 months and 12 months of birth of the subject.

8. The method of claim 1, wherein a 11.3 mg dose of the antisense oligonucleotide is administered in a volume of 4.7 mL, and wherein the dose is administered to the subject between 12 months and 24 months of birth of the subject.

9. The method of claim 1, wherein a 12.0 mg dose of the antisense oligonucleotide is administered in a volume of 5 mL, and wherein the dose is administered to the subject after 24 months of birth of the subject.

10. The method of claim 1, comprising administering to the human subject at least two doses wherein the second dose is administered 12-18 days after the first dose.

* * * * *